United States Patent
Shi et al.

(10) Patent No.: US 6,727,068 B2
(45) Date of Patent: Apr. 27, 2004

(54) METHOD FOR NON-REDUNDANT LIBRARY CONSTRUCTION

(75) Inventors: Liang Shi, San Diego, CA (US); Xun Wang, San Diego, CA (US); Bi-Yu Li, San Diego, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 10/055,109

(22) Filed: Jan. 23, 2002

(65) Prior Publication Data

US 2003/0022192 A1 Jan. 30, 2003

Related U.S. Application Data

(60) Provisional application No. 60/263,916, filed on Jan. 24, 2001.

(51) Int. Cl.$^7$ .......................... C12Q 1/68; C12N 15/00; C12N 15/63; C12N 1/20; C07H 21/04
(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2; 536/24.3; 935/6

(56) References Cited

U.S. PATENT DOCUMENTS

| | | | |
|---|---|---|---|
| 5,093,245 A | | 3/1992 | Keith et al. |
| 5,366,877 A | | 11/1994 | Keith |
| 5,420,032 A | * | 5/1995 | Marshall ..................... 435/199 |
| 5,459,037 A | | 10/1995 | Sutcliffe et al. |
| 5,695,937 A | | 12/1997 | Kinzler et al. |
| 5,712,126 A | | 1/1998 | Weissman et al. |
| 5,866,330 A | | 2/1999 | Kinzler et al. |
| 5,871,697 A | | 2/1999 | Rothberg et al. |
| 6,140,086 A | * | 10/2000 | Fox ......................... 435/91.41 |
| 6,340,565 B1 | * | 1/2002 | Oliner ............................ 435/6 |
| 6,372,479 B1 | * | 4/2002 | Jones ...................... 435/252.3 |

FOREIGN PATENT DOCUMENTS

| | | |
|---|---|---|
| WO | WO 98/31838 | 7/1998 |
| WO | WO 98/51789 * | 11/1998 ..................... 435/6 |
| WO | WO 98/51789 A2 A3 | 11/1998 |
| WO | WO 01/27329 | 4/2001 |

OTHER PUBLICATIONS

Adams et al., "Complementary DNA sequencing: Expressed sequence tags and human genome project." *Science* 252:1651–1656, (1991).
Dempsey et al., "A cardiovascular EST repertoire: progress and promise for understanding cardiovascular disease." *Mol. Med. Today* 6:231–237, (2000).
Fishel et al., "The human mutator gene homolog MSH2 and its association with hereditary nonpolyposis colon cancer." *Cell* 75:1027–1038, (1993).
Graves, D., "Powerful tools for genetic analysis come of age." *Trends Biotechnol.* 17:127–134, (1999).
Gubler et al., "A simple and very efficient method for generating cDNA libraries." *Gene* 25:263–269, (1983).
Karp, P., "Database links are a foundation for interoperability." *Trends Biotechnol.* 14:273–279, 1996.
Koyama et al., "Structure of a cytotoxic T–lymphocyte–specific gene shows a strong homology to fibrinogen β and γ chains." *Proc. Natl. Acad. Sci. USA* 84:1609–1613, (1987).
Levy–Lahad et al., "A familial Alzheimer's disease locus on chromosome I." *Science* 269:970–977, (1995).
Pan et al., "The receptor for the cytotoxic ligand TRAIL." *Science* 276:111–113, (1997).
Papadopoulos et al., "Mutation of mutL homolog in hereditary colon cancer." *Science* 263:1625–1629, (1994).
Richmond et al., "Chasing the dream: plant EST microarrays." *Curr. Opin. Plant Biol.* 3:108–116, (2000).
Sheridan et al., "Control of TRAIL–induced apoptosis by a family of signaling and decoy receptors." *Science* 277:818–821, (1997).
Strausberg et al., "The Cancer Genome Anatomy Project: building an annotated gene index." *Trends Genet.* 16(3):103–106, (2000).
Vincenz et al, "Fas–associated death domain protein interleukin–1β–converting enzyme 2 (FLICE2), an ICE/Ced–3 homologue, is proximally involved in CD95– and p55–mediated death signaling." *J. Biol. Chem.* 272(10):6578–6583, (1997).
Yamamoto et al., "Use of serial analysis of gene expression (SAGE) technology." *J. Immunol. Meth.* 250:45–66, (2001).
Zipfel et al., "Complexity of the primary genetic response to mitogenic activation of human T cells." *Mol. Cell. Biol.* 9(3):1041–1048, (1989).
Zweiger et al., "From expressed sequence tags to 'epigemonics': an understanding of disease processes." *Curr. Opin. Biotechnol.* 8:684–687, (1997).
Vos P., et al. "AFLP: A new technique for DNA fingerprinting", *Nucleic Acids Research* 23 (21):4407–4414 (1995).
Wurff Van Der Awg, et al., "TE–AFLP: Combining rapidity and robustness in DNA fingerprinting", *Nucleic Acids Research* 28 (24):e105 (1–5) (2000).
Wang, Aijin, et al., "Rapid analysis of gene expression (RAGE) facilitates universal expression profiling" *Nucleic Acids Research* 27 (23):4609–4618 (1999).
Li, Bu-yu et al. "Analysis of Differential Gene expression by ligation specificity–based transcript profiling", *OMICS A Journal of Integrative Biology* 6 (2):175–185 (2002).

* cited by examiner

*Primary Examiner*—Kenneth R. Horlick
(74) *Attorney, Agent, or Firm*—Mary Kakefuda

(57) ABSTRACT

Provided are novel methods for the production of nucleic acid libraries having reduced redundancy. Also provided are methods for determination of changes in RNA expression associated with pathological conditions, and physiological or developmental state. Additional aspects provided non-redundant tags or probes produced by the disclosed methods and microarrays incorporating such tags.

43 Claims, 3 Drawing Sheets

METHOD FOR NON-REDUNDANT LIBRARY CONSTRUCTION

CROSS REFERENCE TO RELATED APPLICATIONS

This application claims the benefit of U.S. Provisional Patent Application Ser. No. 60/263,916, filed Jan. 24, 2001 now abandoned, which is herein incorporated by reference in its entirety for all purposes.

BACKGROUND

The field of genomics has taken rapid strides in recent years. It started with efforts to determine the entire nucleotide sequence of simpler organisms such as viruses and bacteria. As a result, genomic sequences of *Hemophilus influenzae* (Fleischman et al., *Science* 269: 496–512, 1995) and a number of other bacterial strains (*Escherichia coli, Mycobacterium tuberculosis, Helicobacter pylori, Caulobacter jejuni, Mycobacterium leprae*) are now available (reviewed in Nierman et al., *Curr. Opin. Struct. Biol.* 10: 343–348, 2000). This was followed by the determination of complete nucleotide sequence of a number of eukaryotic organisms including budding-yeast (*Saccharomyces cerevisiae*) (Goffeau et al., *Science* 274: 563–567, 1996), nematode (*Cenorhabditis elegans*) (*C. elegans* sequencing consortium, *Science* 282: 2012–2018 1998) and fruit fly (*Drosophila melanogaster*) (Adams et al., *Science* 287: 2185–2195, 2000). The sequence of the human genome was published in February of 2001 (International Human Genome Sequence Consortium, *Nature,* 409:860–921, 2001; Venter et al., *Science,* 291:1304–1351, 2001). Additionally, some of the ongoing efforts are currently focused on genome sequencing of agriculturally important plants such as rice (*Science* 288: 239–240, 2000; Sasaki and Burr, *Curr. Opin. Plant Biol.* 3: 138–141, 2000) and experimentally critical animal model such as mice (News Focus, *Science* 288: 248–257, 2000).

The availability of complete genomic sequences of various organisms promises to significantly advance our understanding of various fundamental aspects of biology. It also promises to provide unparalleled applied benefits such as understanding genetic basis of certain diseases, providing new targets for therapeutic intervention, developing a new generation of diagnostic tests, etc. New and improved tools, however, will be needed to harvest and fully realize the potential of genomics research.

Even though the DNA complement or gene complement is identical in various cells in the body of multi-cellular organisms, there are qualitative and quantitative differences in gene expression in various cells. A human genome is estimated to contain roughly about 30,000–40,000 genes, however, only a fraction of these genes are expressed in a given cell (International Human Genome Sequence Consortium, *Nature,* 409:860–921, 2001; Venter et al., *Science,* 291:1304–1351, 2001). Moreover, there are quantitative differences among the expressed genes in various cell types. Although all cells express certain housekeeping genes, each distinct cell type additionally expresses a unique set of genes. Phenotypic differences between cell types are largely determined by the complement of proteins that are uniquely expressed. It is the expression of this unique set of genes and their encoded proteins, which constitutes functional identity of a cell type, and distinguishes it from other cell types. Moreover, the complement of genes that are expressed, and their level of expression vary considerably depending on the developmental stage of a given cell type. Certain genes are specifically activated or repressed during differentiation of a cell. The level of expression also changes during development and differentiation. Qualitative and quantitative changes in gene expression also take place during cell division, e.g. in various phases of cell cycle. Signal transduction by biologically active molecules such as hormones, growth factors and cytokines often involves modulation of gene expression. Global change in gene expression also plays a determinative role in the process of aging.

In addition to the endogenous or internal factors mentioned above, certain external factors or stimuli, such as environmental factors, also bring about changes in gene expression profiles. Infectious organisms such as bacteria, viruses, fungi and parasites interact with the cells and influence the qualitative and quantitative aspects of gene expression. Thus, the precise complement of genes expressed by a given cell type is influenced by a number of endogenous and exogenous factors. The outcome of these changes is critical for normal cell survival, growth, development and response to the environment. Therefore, it is important to identify, characterize and measure changes in gene expression. The knowledge gained from such analysis will not only further our understanding of basic biology, but it will also allow us to exploit it for various purposes such as diagnosis of infectious and non-infectious diseases, screening to identify and develop new drugs, etc.

Besides the conventional, one by one gene expression analysis methods like Northern analysis, RNase protection assays, and real time PCT (RT-PCR); there are several methods currently available to examine gene expression in a genome wide scale. These approaches are variously referred to as RNA profiling, differential display, etc. These methods can be broadly divided into three categories: (1) hybridization-based methods such as subtractive hybridization (Koyama et al., *Proc. Natl. Acad. Sci. USA* 84: 1609–1613, 1987; Zipfel et al., *Mol. Cell. Biol.* 9: 1041–1048, 1989), microarray, etc., (2) cDNA tags: EST, serial analysis of gene expression (SAGE) (see, e.g. U.S. Pat. Nos. 5,695,937 and 5,866,330), and (3) fragment size based, often referred to as gel-based methods where a differential display is generated upon electrophoretic separation of DNA fragments on a gel such as a polyacrylamide gel (described in U.S. Pat. Nos. 5,871,697, 5,459,037, 5,712,126 and PCT publication No. WO 98/51789).

Expressed Sequence Tags (ESTs) are created by partially sequencing (usually a single pass) randomly chosen gene transcripts that have been converted into cDNA. The concept of ESTs as an alternative to genome sequencing for the rapid determination of the expressed complement of a genome was first introduced by Adams et al. (*Science* 252: 1651–1656, 1991). The EST approach, combined with the power of high throughput sequencing, has brought about a revolution (Zweiger and Scott, *Curr. Opin. Biotechnol.* 8: 684–687, 1997). EST tags often contain enough information to identify the transcript corresponding to the cDNA clone by searching nucleotide and protein databases. Thus, the EST approach provides a valuable tool for the identification and characterization of novel genes. ESTs are also long enough to be reliably used as substrate for microarrays, and are less expensive and superior in performance than oligonucleotides for the purpose. The use of EST-based microarray technology is finding increasing use in global genome wide transcript profiling. The number of EST sequences being deposited in databanks is exponentially growing. A sub-database containing EST sequences (dbEST) is available in GenBank. A large number of EST sequences from various organisms are also available in public databanks.

The National Cancer Institute (NCI) launched the first large-scale EST project in 1997, the Cancer Genome Anatomy Program (CGAP), focusing on a single aspect, the comprehensive molecular characterization of human normal, pre-cancerous and malignant cells (Strausberg et al., *Trends Genet.* 16: 103–106, 2000). Similarly, tissue-specific EST databases have also been created in order to understand the unique physiological functions of a tissue/organ as well as to gain insight into changes into global gene expression associated with various pathological conditions. For instance, a collection of EST sequences derived from human heart tissue of various anatomical, developmental and pathological stages has been established with a view to understand cardiovascular diseases (Dempsey et al., *Mol. Med. Today*, 6: 231–237, 2000). The EST profile of an organ typically reflects the unique function of the organ. For example, the pancreas and liver have a large proportion of ESTs corresponding to secreted proteins, whereas the brain and heart have a very small proportion of such ESTs. Similarly, ESTs corresponding to contractile proteins are present in high proportion in the heart, but are absent in the brain, liver or pancreas. A number of EST projects directed at agriculturally important plants such as rice, wheat, maize, soybean, and sorghum are currently underway (Richmond and Somerville, *Curr. Opin. Plant Biol.*, 3: 108–116, 2000).

One of the most fundamental applications of an EST approach has been in the rapid identification of novel gene homologs and orthologs. The successful implementation of this approach is illustrated by the discovery of a number of novel members of the chemokine family (Karp, *Trends Biotechnol.* 14: 273–279, 1996) and the TNFα and TNFα receptor families (Pan et al., *Science* 276: 111–113, 1997; Sheridan et al., *Science* 277:818–821, 1997; Vincez and Dixit, *J. Biol. Chem.* 272: 6578–6583, 1997). Major advances in bioinformatic software used for mining the rapidly growing relational databases, including more powerful motif identification and search tools, have accelerated the pace of progress in the use of EST approach for the identification of new genes (Zweiger and Scott, supra). Availability of a human transcript chromosomal map showing map positions of an increasing number of ESTs has significantly helped accelerate the progress in the field of positional cloning of genes, particularly in the identification and characterization of gene mutations or alterations which cause or predispose an individual to a particular disease or trait. Once a genetic locus for a disease is identified by genetic linkage analysis, the presence of ESTs in the region surrounding the locus provides a list of genes likely responsible for the disease. This strategy has been used successfully in the identification of presenilin 2 implicated in Alzheimer's disease (Levy-Lahad et al., *Science* 269: 970–973 and 973–977, 1995), and mutS homolog 2 implicated in hereditary colon cancer (Fishel et al., *Cell* 75: 1027–1038, 1993; Papadopoulos et al., *Science* 263: 1625–1629, 1994).

Another major use of ESTs is in the large-scale monitoring of gene expression of a given cell type under various physiological, pathological or environmental conditions. Not only does this yield valuable information about the fundamental biological processes, but it also promises to provide important targets for therapeutic intervention in various diseases. ESTs in the form of PCR products provide a better and cost effective alternative to the use of oligonucleotides for use in microarray-based gene expression analysis. In this method, a large number of ESTs are gridded on a solid support, such as glass or a polymer, which can be hybridized to fluorescently tagged samples of mRNA or cDNA derived from a given cellular source (Graves, *Trends Biotechnol.* 17: 127–134, 1999). The hybridization is scored qualitatively and quantitatively by a scanning fluorescent microscope. Since the sequence and location of the immobilized probes is known, the technique provides a rapid and comprehensive analysis of gene expression, and essentially creates a transcript profile of the target cell. In a variation of the theme, a collection of ESTs with unknown sequences can also be used to prepare a microarray, and only the EST clones of relevance (e.g. showing significant change in expression levels) are then sequenced.

Microarray based gene analysis approach enables working with hundreds of thousands of genes simultaneously rather than one or a few genes at a time. Microarray technology has come at an appropriate time, when entire genomes of humans and other organisms are being worked out. Massive sequence information generated as a result of genome sequencing, particularly human genome sequencing, has created a demand for technologies that provide high-throughput and speed. Microarrays fill this unique niche. Most of the complex physiological processes precede or succeed change in the expression of a large number of genes. Techniques that were available before the advent of microarrays are not suitable to monitor such large-scale changes in gene expression. DNA microarrays offer the opportunity to perform fast, comprehensive, moderately quantitative analyses on hundreds of thousands of genes simultaneously. A DNA microarray is composed of an ordered set of DNA molecules of known sequences usually arranged in rectangular configuration in a small space such as 1 $cm^2$ in a standard microscope slide format. For example, an array of 200×200 would contain 40,000 spots with each spot corresponding to a probe of known sequence. Such a microarray can be potentially used to simultaneously monitor the expression of 40,000 genes in a given cell type under various conditions. The probes usually take the form of cDNA, ESTs or oligonucleotides. Most preferred are ESTs and oligonucleotides in the range of 30–200 bases long as they provide an ideal substrate for hybridization. There are two approaches to building these microarrays, also known as chips, one involving covalent attachment of pre-synthesized probes, the other involving building or synthesizing probes directly on the chip. The sample or test material usually consists of RNA that has been amplified by PCR. PCR serves the dual purposes of amplifying the starting material as well as allowing introduction of fluorescent tags. For a detailed discussion of microarray technology, see e.g., Graves, *Trends Biotechnol.* 17: 127–134, 1999.

High-density microarrays are built by depositing an extremely minute quantity of DNA solutions at precise location on an array using high precision machines, a number of which are available commercially. An alternative approach pioneered by Packard Instruments, enables deposition of DNA in much the same way that ink jet printer deposits spots on paper. High-density DNA microarrays are commercially available from a number of sources such as Affymetrix, Incyte, Mergen, Genemed Molecular Biochemicals, Sequenom, Genomic Solutions, Clontech, Research Genetics, Operon and Stratagene. Currently, labeling for DNA microarray analysis involves fluorescence, which allows multiple independent signals to be read at the same time. This allows simultaneous hybridization of the same chip with two samples labeled with different fluorescent dyes. The calculation of the ratio of fluorescence at each spot allows determination of the relative change in the expression of each gene under two different conditions. For example, comparison between a normal tissue and a corresponding tumor tissue using the approach helps in identifying genes whose expression is significantly altered. Thus, the method offers a particularly powerful tool when the gene expression profile of the same cell is to be compared under two or more conditions. High-resolution scanners with capability to monitor fluorescence at various wavelengths are commercially available.

Although the EST approach is a powerful tool in the study of expression and function of genes, a major drawback of this method is the unavoidable redundancy of clones representing highly expressed transcripts and conversely under-representation of transcripts with low expression levels. The problem persists even with normalized and subtractive libraries. In order to sample the low-level transcripts, the sequencing effort must go very deep into the library which involves substantial labor, time, and associated costs. SAGE greatly minimizes the sequencing runs, but generates cDNA tags (13–15 bases) that are too short to be used as gene specific primers or probes. Moreover, SAGE suffers from higher cost and labor intensiveness.

Accordingly, there is a need for further improvements in the techniques used to identify, sequence and characterize novel genes.

SUMMARY

The present inventors have discovered a novel method for the production of a nucleic acid library, in particular a non-redundant nucleic acid library, and more particularly a non-redundant, expressed sequence tag (EST) library. Among the several advantages of the present method over the prior art are decreased redundancy resulting in increased speed and decreased cost in library construction, the representation of transcripts independent of their expression level, and the ability to isolate and sequence transcripts without cloning.

According, one of the several aspects of the invention provides a method for constructing a nucleic acid library comprising obtaining a population of double-stranded cDNA containing a detectable label. In one embodiment, the detectable label is on the 3' end and the cDNA is produced by isolating polyA mRNA, hybridizing the polyA mRNA to an oligo dT primer with a 5' label, synthesizing the first cDNA strand by primer extension and synthesizing the second cDNA strand by nick translation. The end-labeled cDNA is divided into portions, for example a first portion and a second portion. The first portion is digested with at least one sequence-specific restriction endonuclease and the second portion is digested with at least one restriction endonuclease having a degenerate recognition sequence. Any number of sequence-specific endonucleases can be used but commonly at least 4 to 6 are used. Endonucleases having 4-base, 5-base, or 6-base recognition sequences can be used as well as combinations of endonuclease having recognition sequences of different lengths. In one embodiment, the at least one endonuclease having a degenerate recognition sequence produces fragments having an unpaired (single-stranded) overhang containing $N^m$ sequences where N is the extent of degeneracy and is an integer between 2 and 4, and m is the number of bases in the unpaired overhang and is generally an integer between 2 and 6. In one embodiment, $N^m$ equals at least 64.

After the first digestion, the labeled digestion fragments in each portion are isolated by the detectable label and the isolated fragments subjected to a second digestion. In the second digestion, portion one is digested with the at least one restriction endonuclease having a degenerate recognition sequence previously used to digest portion two, and portion two is digested with the at least one sequence specific endonuclease previously used to digest portion one. Following this second digestion, fragments containing the detectable label are separated and discarded while unlabeled fragments are retained.

The retained unlabeled fragments are then hybridized and ligated to adapters specific for the endonucleases used. In one embodiment, the portions are combined prior to adaptor hybridization and ligation, while in another embodiment, the portions are kept separate. Generally, adapters for all possible fragments produced will be used. Thus, if an endonuclease potentially produces 64 different fragments (e.g. different unpaired overhangs), then 64 different adapters are used for that endonuclease. Ordinarily, the adapters are designed so that they do not have high sequence homology to any known sequences in the population. In one embodiment, adapters are designed so that they have common regions that can be used for primer binding sites. In one embodiment, no more than 10 different primer binding sequences are used while in another embodiment, two different primer binding sequences are used.

Following addition of the adapters, the fragments are amplified, ordinarily by PCR and generally using primer binding sites contained in the adapters. After, amplification, the fragments produced are separated and identified. In one embodiment, the fragments produced are identified by separating them on the basis of size. In another embodiment, the amount of each fragment produced is quantified.

Another aspect provides a method for detecting a change in RNA expression in a tissue or cell associated with an internal or external factor. In one embodiment, a population of double-stranded cDNA having an end label is produced from RNA obtained from a first cell or tissue exposed to the internal or external factor of interest and a nucleic acid library constructed using any of the novel methods described herein. The number of fragments and/or quantity of each fragment in the library is then determined to establish the pattern of RNA expression. Next a population of double stranded cDNA having an end labeled is produced from RNA obtained from a second cell or tissue not exposed to the internal or external factor of interest and a nucleic acid library produced as for the first cell or tissue. The number of fragments and/or quantity of each fragment in the library is determined to establish the pattern of RNA expression. The two patterns can then be compared to determine the effect of the external or internal factor on RNA (gene) expression. In one embodiment, data representing the pattern of RNA expression for the cell or tissue not exposed to the internal or external factor is stored on a computer-readable medium.

Still another aspect provides a method for diagnosing a disease, condition, disorder, or predisposition where the disease, condition, disorder or predisposition is associated with a change in RNA expression. In one embodiment, a population of double-stranded cDNA having an end label is produced from RNA obtained from a first cell or tissue known to have the disease, condition, disorder or predisposition of interest and a nucleic acid library constructed using any of the novel methods described herein. The number of fragments and/or quantity of each fragment in the library is then determined to establish the pattern of RNA expression. Next a population of double stranded cDNA having an end label is produced from RNA obtained from a second cell or tissue from a test subject and a nucleic acid library produced as for the first cell or tissue. In one embodiment, the first and second cell or tissue are of the same type. In another embodiment, the first and second cell or tissue are from the same species. The number of fragments and/or quantity of each fragment in the library is determined to establish the pattern of RNA expression. The two patterns can then be compared to diagnose the disease, condition, disorder or predisposition. In one embodiment, data representing the pattern of RNA expression for the cell or tissue known to have the disease, condition, disorder or predisposition of interest is stored on a computer-readable medium.

A further aspect provides a method for determining the physiological or developmental state of a cell or tissue. In one embodiment, a population of double-stranded cDNA having an end label is produced from RNA obtained from a first cell or tissue of a known physiological or developmental state and a nucleic acid library constructed using any of the novel methods described herein. The number of fragments and/or quantity of each fragment in the library is then determined to establish the pattern of RNA expression. Next a population of double stranded cDNA having an end labeled is produced from RNA obtained from a second cell or tissue of an unknown physiological or developmental state and a nucleic acid library produced as for the first cell or tissue. In one embodiment, the first and second cell or tissue are of the same type. In another embodiment, the first and second cell or tissue are from the same species. The number of fragments and/or quantity of each fragment in the library is determined to establish the pattern of RNA expression. The two patterns can then be compared to determine the physiological or developmental state of the cell or tissue. In one embodiment, data representing the pattern of RNA expression for the cell or tissue of a known physiological or developmental state is stored on a computer-readable medium.

Another aspect provides a method for constructing a nucleic acid expression library comprising obtaining a population of double-stranded cDNA molecules that contain a detectable label on their 3' ends. The population of cDNA molecules is then digested with at least one restriction endonuclease having a degenerate recognition sequence containing at least one degenerate base to produce digestion fragments. The digestion creates single-stranded (unpaired) overhangs or portions in the fragments. These unpaired overhangs contain a region having the formula $N^m$, where N is the extent of degeneracy and m is the number of bases. The fragments are then hybridized and ligated to a population of adapters, where the adapters are specific for the at least one endonuclease used. In one embodiment, adapters are provided for all possible fragments (different overhangs). In another embodiment, less than all possible adapters are used. In one embodiment $N^m$ equals at least 16, while in another embodiment, the adapters contain a primer binding region(s) common to groups of adapters or to all adaptors.

After ligation of the adapters, the 3' end fragments produced are isolated using the detectable label. The 3' end labeled fragments are then amplified and the amplified fragments are identified. In one embodiment the fragments are amplified by PCR while in a related embodiment, the amplification uses primer binding sites in the adapters. In still another embodiment, the amplified 3' end fragments are identified by separating them on the basis of size.

Yet a further aspect provides a computer readable medium having stored thereon executable instructions for performing a method comprising, receiving data on RNA expression from a first cell or tissue produced by any of the novel methods disclosed herein and comparing the data from the first cell or tissue with RNA expression data produced from a second cell or tissue using the same method for determining RNA expression as for the first cell or tissue.

Another aspect provides non-redundant expressed sequence tags or probes comprising the fragments or portions thereof produced by the novel methods disclosed herein. Such probes or tags can be used, for example, to determine gene expression by Northern blotting.

Yet another aspect provides microarrays containing fragments or portions thereof produced by the novel methods disclosed herein.

BRIEF DESCRIPTION OF THE FIGURES

These and other features, aspects, and advantages of the present invention will become better understood with regard to the following description, appended claims and accompanying figures where:

DETAILED DESCRIPTION

Figure 1:
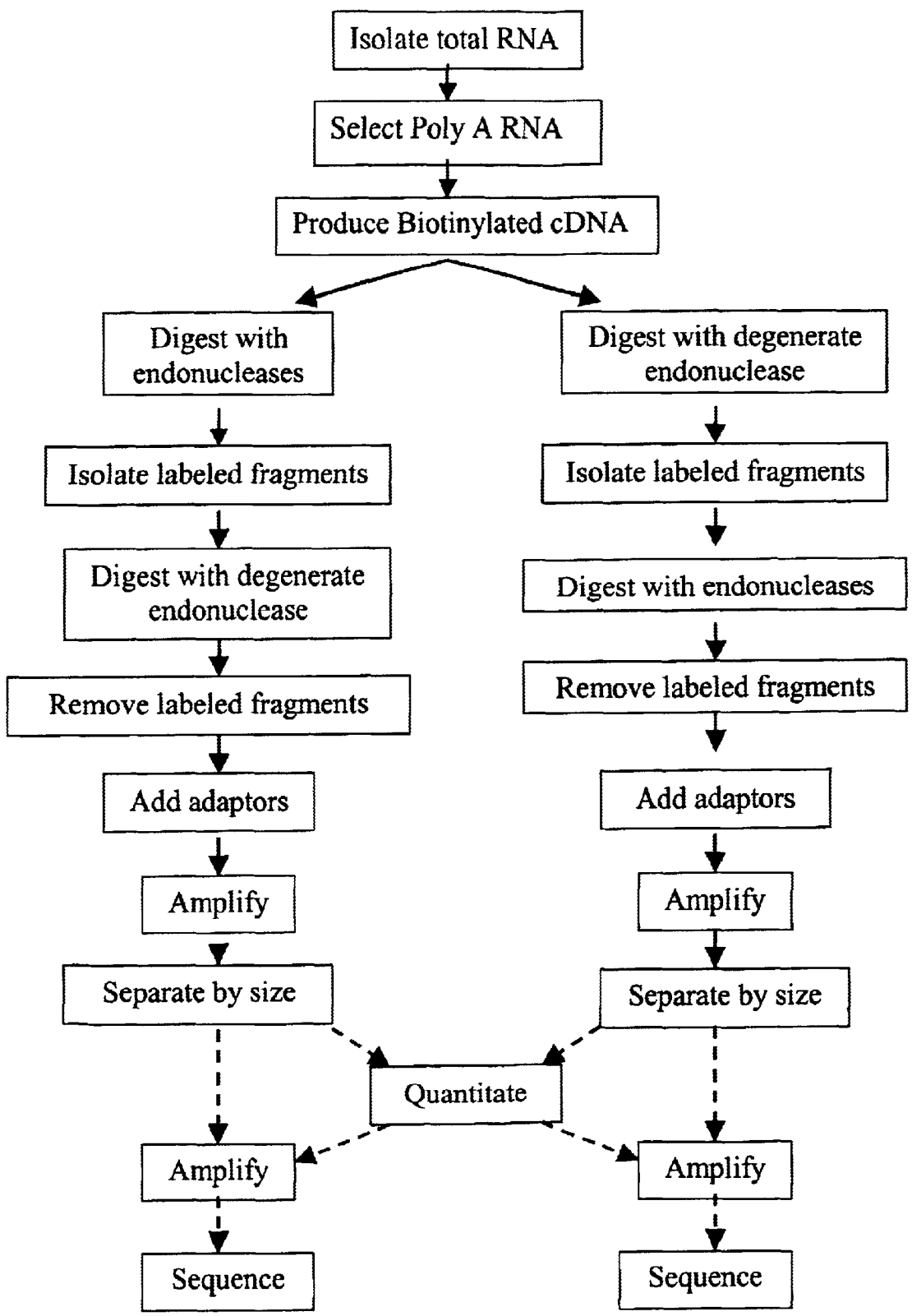
FIG. 1 shows a schematic representation of one embodiment of the disclosed method using two digestions. Arrows with broken lines indicate optional steps.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, public databases, public database entries and other references cited in this application are herein incorporated by reference in their entirety as if each individual publication, patent, patent application, public database, public database entry or other reference were specifically and individually indicated to be incorporated by reference.

The inventive discovery disclosed herein provides, in part, a new and versatile method for the construction of a cDNA library, and more particularly a library that is substantially free of redundancy (a non-redundant library). In one embodiment, the method is used to construct a non-redundant EST library. Advances of the present invention over the prior art include, but are not limited to, the avoidance of substantial redundancy so that, ideally, each expressed gene is represented by a single sequence. In addition, in contrast to previous methods, the present method allows for the representation of polynucleotide sequences independent of their level of expression, so that rare transcripts are as likely as common transcripts to be represented in the resulting library. The present method also allows for the isolation and direct sequencing of transcripts, including EST fragments, without the need of cloning. Because of the lack of redundancy, the use of the methods disclosed herein results in the need to sequence considerably less sequences to cover the entire spectrum of transcripts, thus greatly decreasing the time and expense associated with library construction using traditional methods. The present inventive discovery has broad application including, but not limited to, non-redundant EST library construction, microarrays, diagnostics, gene expression studies, and establishment of non-redundant gene tags.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes peptide nucleic acids such as polymeric nucleotides containing neutral amide backbone linkages composed of aminoethyl glycine units (Nielsen et al., *Science*, 254:1497, 1991). This term refers only to the primary structure of the molecule. Thus, this term includes double- and single-stranded DNA and RNA as well DNA/RNA hybrids that may be single-stranded, but are more typically double-stranded. In addition, the term also refers to triple-stranded regions comprising RNA or DNA or both RNA and DNA. The strands in such regions may be from the same molecule or from different molecules. The regions may include all or one or more of the molecules, but more typically involve only a region of some of the molecules. The terms also include known types of modifications, for example, labels, methylation, "caps", substitution of one or more of the naturally occurring nucleotides with an analog, internucleotide modifications such as, for example, those with uncharged linkages (e.g. methyl phosphonates, phophotriesters, phosphoamidates, carbamates etc.), those containing pendant moieties, such as, for example, proteins (including for e.g., nucleases, toxins, antibodies, signal peptides, poly-L-lysine, etc.), those with intercalators (e.g., acridine, psoralen, etc,), those containing alkylators, those with modified linkages (e.g. alpha anomeric nucleic acids, etc.), as well as unmodified forms of the polynucleotide. Polynucleotides include both sense and antisense, or coding and template strands. The terms include naturally occurring and chemically synthesized molecules.

The terms "endonuclease", "restriction endonuclease" and "restriction enzyme" are used interchangeably and in the broadest sense, refer to an enzyme that recognizes a double-stranded DNA sequence-specifically and cuts it endonucleotically. It is noted that when a restriction endonuclease is referred to as a "four-base cutter", "six-base cutter", etc. reference is made to the number of nucleotide bases within the recognition sequence of such restriction endonuclease, not including degeneracy, if any. For example, a restriction endonuclease that has the degenerate recognition sequence CCNNGG, where "N" represents two or more of nucleotides A, G, C or T, would be referred to as a "four-base cutter". Digestion with a "four-base cutter" restriction endonuclease will result in one cut approximately every 256 ($4^4$) bases of the polynucleotide digested, while digestion with a "five-base cutter" restriction endonuclease will result in one cut approximately every 1024 ($4^5$) bases, etc. Accordingly, one factor in choosing a restriction endonuclease will be the desired size and the number of the restriction endonuclease fragments for any particular application. Selection of appropriate restriction endonucleases can be made by one of ordinary skill in the art without undue experimentation.

A restriction endonuclease with a "degenerate recognition sequence" is one that has one or more degenerate bases in the sequence recognized by such restriction endonuclease, or in the overhang produced by such restriction endonuclease. In this context, the term "degenerate base" means that any of the four bases (A, C, G or T/U) or a specific subset of four bases (2–3) may be present at the indicated position. The term "number of degenerate bases" refers to the number of nucleotide positions within the recognition or cleavage sequence that may be occupied by degenerate bases. The term "extent of degeneracy" refers to the number of bases that can occupy a given nucleotide position in the recognition or cleavage sequence of a restriction enzyme without significantly affecting the enzymatic activity of such endonuclease. "Full degeneracy" results when any of the four bases (A, C, G or T/U) can occupy a given degenerate position in the recognition or cleavage sequence. Accordingly, "partial degeneracy" results when a given degenerate position can be occupied by a specific subset of four bases (2–3) such as A/G, C/T, A/C/G or A/T/G etc. Standard nomenclature found in WIPO Standard ST.25 (1998) is used herein to represent degeneracy such that r=g or a, y=t/u or c, m=a or c, k=g or t/u, s=g or c, w=a or t/u, b=g or c or t/u, d=a or g or t/u, h=a or c or t/u, v=a or g or c, and n=a or g or c or t/u.

A "sequence specific endonuclease" is a restriction endonuclease in which no degenerate bases are present in the sequence recognized by such restriction endonucleases.

The terms "internal factors" and "endogenous factors" are used interchangeably, and refer to factors or changes brought about internally, i.e. from within the organism, and include, for example, differences in genetic background and various physiological or pathological changes such as those accompanying growth, development, differentiation, cell cycle, signal transduction, and action of biologically active molecules, for instance hormones, growth factors and cytokines. The terms "external factors" and "exogenous factors" are used interchangeably and refer to factors or changes brought about externally, i.e. from outside the organism, and include, for example, infection by pathogens such as bacteria, viruses, fungi, or insects, and environmental changes such as toxins, heat, radiation, drought, salinity etc.

As used herein, "subject" refers to the source of the cell or tissue used and includes, plants, animals and human beings.

The term "detectable label" refers to a label which when attached, preferably covalently, provides a means of detection. There are a wide variety of labels available for this purpose including, without limitation, radioactive labels such as radionuclides, fluorophores or fluorochromes, peptides, enzymes, antigens, antibodies, vitamins or steroids. For example, radioactive nuclides such as $^{32}$P or $^{35}$S, or fluorescent dyes are conventionally used to label PCR primers. Chemiluminescent dyes can also be used for the purpose. Non-limiting examples of some commonly used fluorescent dyes are listed in Table 1. The label can be attached directly to the molecule of interest, be attached through a linker, or be located on a particle such as a microbead.

As used herein "sequence" means the linear order in which monomers occur in a polymer, for example, the order of amino acids in a polypeptide or the order of nucleotides in a polynucleotide.

As used herein, the term "animal" includes human beings.

The present discovery provides a novel combination of sequence specific endonucleases and endonuclease with degenerate recognition sequences along with sequence specific adapters to produce nucleic acid libraries with substantially reduced redundancy. By substantially reduced redundancy is meant that the libraries produced by the present method have ordinarily less than 50% redundancy, more ordinarily less than 40% redundancy, generally less than 30% redundancy, more generally less than 20% redundancy, often less than 15% redundancy, more often less than 10% redundancy, preferably less than 5% redundancy, more preferably less than 2% redundancy and more preferably still, less than 1% redundancy. By redundancy is meant that the sequence is represented more than once in the library.

In one embodiment, a population of end-labeled polynucleotides is obtained. Any label which can be used to separate labeled from non-labeled polynucleotides can be used. In one embodiment, the label is biotin. The label can be located on the 3' or 5' end of the polynucleotide. In one embodiment the label is located on the 3' end. If the polynucleotide is double-stranded, the label may be on either the coding (plus) or non-coding (template or minus) strand. In describing double stranded polynucleotides, the designation of the 3' or 5' end of the molecules refers to the coding or plus strand. Thus in a 3' end labeled double-stranded polynucleotide, the label can be present on the 3' end of the coding strand or the 5' end of the template strand.

The polynucleotides can be DNA or RNA. For example, genomic DNA or cDNA made from RNA can be used. In one embodiment, the population of polynucleotides can comprise double stranded cDNA. The cDNA can be produced from RNA, mRNA or polyA mRNA using methods found in standard molecular biology references such as Ausubel et al., eds., *Short Protocols in Molecular Biology*, $3^{rd}$ ed., Wiley, 1995; and Sambrook et al., *Molecular Cloning*, $2^{nd}$ ed., Cold Spring Laboratory Press, 1989. For example, in one embodiment cDNA is produced from polyA mRNA. In this embodiment, total RNA is isolated from the cells or tissues of interest. Any cell or tissue containing polyA mRNA can by used including cells and tissue obtained from bacteria, fungi, plants and animals. By "tissue" is meant a plurality of cells that in their native state are organized to perform one or more specific functions. Non-limiting examples include muscle tissue, cardiac tissue, nervous tissue, leaf tissue, stem tissue, root tissue, etc. Using standard methods well known in the art, total RNA is isolated from the cells or tissues of interest. The RNA can be used for first strand cDNA synthesis without further purification or polyA mRNA can be isolated using standard methologies. First strand synthesis can be accomplished using standard methodologies such as oligo dT or random hexamer priming. In one embodiment, the polyA mRNA is added to a mixture containing an oligo dT primer, dNTPs, a reverse transcriptase and other necessary ingredients under conditions that allow for first strand cDNA synthesis by primer extension. As will be clear to one of ordinary skill in the art, the exact conditions necessary for first strand synthesis will vary with factors such as the reverse transcriptase used, but such conditions are readily determined without undue experimentation. Any reverse transcriptase capable of producing a cDNA molecule such as avian myeloblastosis viral (AMV) reverse transcriptase or Moloney murine leukemia virus (MMLV) reverse transcriptase can be used. Reverse transcriptases that lack or have reduced RNase H activity may be favorably employed in the present method. In one embodiment the primer has the sequence 5' $L(T)_xVN$ where x is an integer between 4 and 200 and L is a suitable label, such as biotin. In another embodiment, the primer is a labeled primer having the sequence 5' $Seq_1 (T)_xVN$, where $Seq_1$ is a specifically designed anchor sequence. The use of a primer with a VN 3' end ensures that the primer binds at the start of the polyA tail. In addition, the degeneracy results in the production of 12 subpopulations of polynucleotides due to the 12 possible sequences represented by VN ($3^1 \times 4^1$).

Following first strand synthesis, second strand synthesis is accomplished using the first strand cDNA as a template. Second strand synthesis may be carried out using random primers or by nick translation (Gubler and Hoffman, *Gene*, 25:263, 1983). In one embodiment, second strand synthesis is by nick translation. In this embodiment, the DNA/RNA hybrid produced is contacted with a reaction mixture containing a DNA polymerase, for example *E. coli* DNA polymerase I, dNTPs and a suitable reaction buffer. Second strand synthesis can be carried out in the same reaction vessel as first strand synthesis. In one embodiment, the reaction mixture also contains a DNA ligase, such as *E. coli* DNA ligase. The reaction mixture can also contain a RNase H, for example, *E. coli* RNase H. The addition of an RNase H is useful when a reverse transcriptase with reduced RNase H activity is used for first strand synthesis. Following second strand production, the resulting double-stranded cDNA is isolated using standard procedures for DNA isolation, such as phenol:chloroform:isoamyl alcohol extraction followed by ethanol precipitation. Ausubel et al., eds., *Short Protocols in Molecular Biology*, $3^{rd}$ ed., Wiley, 1995 and Sambrook et al., *Molecular Cloning*, $2^{nd}$ ed., Cold Spring Laboratory Press, 1989.

In one embodiment in which the primer $L(T)_xVN$ is preferably used, the double stranded cDNA, which is preferably labeled on its 3' end, is divided into at least two portions and subjected to a first endonuclease digestion. The portions will ordinarily, but not necessarily, contain approximately equal amounts of cDNA. In one embodiment, there are two portions, portion I and portion II. In this embodiment, portion I is digested with at least one restriction endonuclease that generates an overhang or protruding single-stranded area at the site of cleavage. In one aspect, the at least one restriction endonuclease used to digest portion I is a sequence specific endonuclease. The single-stranded area can contain from one up to about 10 bases, ordinarily from one to five bases. In one aspect, the overhang contains three or four bases. In one embodiment, portion I is simultaneously digested with at least two restriction endonucleases, in another embodiment at least three, in yet another embodiment at least four, in a further embodiment at least five, and in still another embodiment portion I is simultaneously digested with at least six endonucleases. The endonucelases chosen can be three-base cutters, four-base cutters, five-base cutters, six-base cutters or any combination thereof.

When combinations of endonucleases are used, the enzymes will ordinary, but not necessarily, be present in equal amounts as measured by units of activity. In one embodiment, a combination of 6, six-base cutter restriction endonucleases is used. As discussed herein, the selection of a particular endonuclease or combination of endonucleases will vary according to the number and length of fragments desired. Selection of suitable endonucleases can be accomplished by one of ordinary skill in the art without undue experimentation. Information about endonucleases can be found in standard molecular biology texts such as those cited herein and in publicly available databases such as The Restriction Enzyme Database (rebase) which can be found at http://rebase.neb.com/rebase/.

In this same embodiment, portion II is digested with at least one endonuclease different from that used to digest portion I. In one aspect, the at least one endonuclease has a degenerate recognition sequence. As with the enzyme or enzymes used to digest portion I, the enzyme(s) used to digest portion II preferably generates a single stranded overhang of from one to 10, ordinary one to five bases. The digestion of portion II can proceed simultaneously with the digestion of portion I or be accomplished at a different time. The number of degenerate bases and the extent of degeneracy in the recognition sequence may be varied based on factors such as the complexity of the genome from which the cDNA is obtained. For example, the use of an endonuclease with 1, 2, 3, or 4 fully degenerate bases in the recognition sequence will allow fractionating of the digested DNA into 4 ($X^z$), 16, 64 or 256 pools, respectively, where X is the extent of degeneracy and Z is the number of bases. This can be further fine-tuned by selecting endonucleases with less than full degeneracy (i.e. X=2–3) at one or more of the degenerate bases in the recognition sequence. The enzyme used can be a two-base cutter to a six-base cutter. In one embodiment, portion II is digested with a four-base cutter endonuclease having seven fully degenerate bases in its recognition sequence. In another embodiment, portion II is digested with Bsl I.

As will be apparent to those skilled in the art, the present method is not limited to the use of sequence specific endonucleases to digest portion I and endonucleases with degenerate recognition sequences for the digestion of portion II. Rather it is possible to use only sequence specific endonucleases, only endonucleases having a degenerate recognition sequence, or any combination thereof.

Following the first digestion, fragments corresponding to the ends of the original polynucleotides are isolated. In one embodiment, the 3' end fragments of the original polynucleotides are isolated by capturing the 3' end fragments using the attached label. For example and without limitation, the products of the first digestion can be contacted with a solid substrate to which is attached molecule that selectively binds to the label on the 3' end of the fragment. For example, if the label is biotin, then avidin or streptavidin can be used. In another example, a specific antibody can be used. Many appropriate combinations of labels and capture molecules will be apparent to those skilled in the art. Any suitable solid substrate can be used. Non-limiting examples, include the walls of centrifuge tubes or microtiter plates, membranes, and beads or other particles. The digestion products are contacted with the solid substrate containing the capture molecule for a time sufficient to allow binding of the labeled fragments to the capture molecule. The 3' fragments are then separated from the rest of the digestion products using standard methodologies. For example, where the capture molecule is attached to a microtiter plate, the contents are removed, and optionally, the plate washed. In the case of beads, the beads are separated from the liquid by either centrifugation or magnetic separation, and optionally washed.

After separation of the labeled 3' ends, portions I and II are subjected to a second restriction enzyme digestion. In one embodiment, the second digestion is a reciprocal digestion; that is, portion I is treated with the same enzymes or combination of enzymes previously used for the first digestion of portion II and vice versa. For example, in the case where the labeled 3' fragments are captured on a solid substrate, the substrate containing the fragments is treated with the endonuclease or combination of endonucleases. Following the second digestion, the liquid containing the products of the second digestion are separated from the solid substrate to which the label remains attached.

Figure 2:
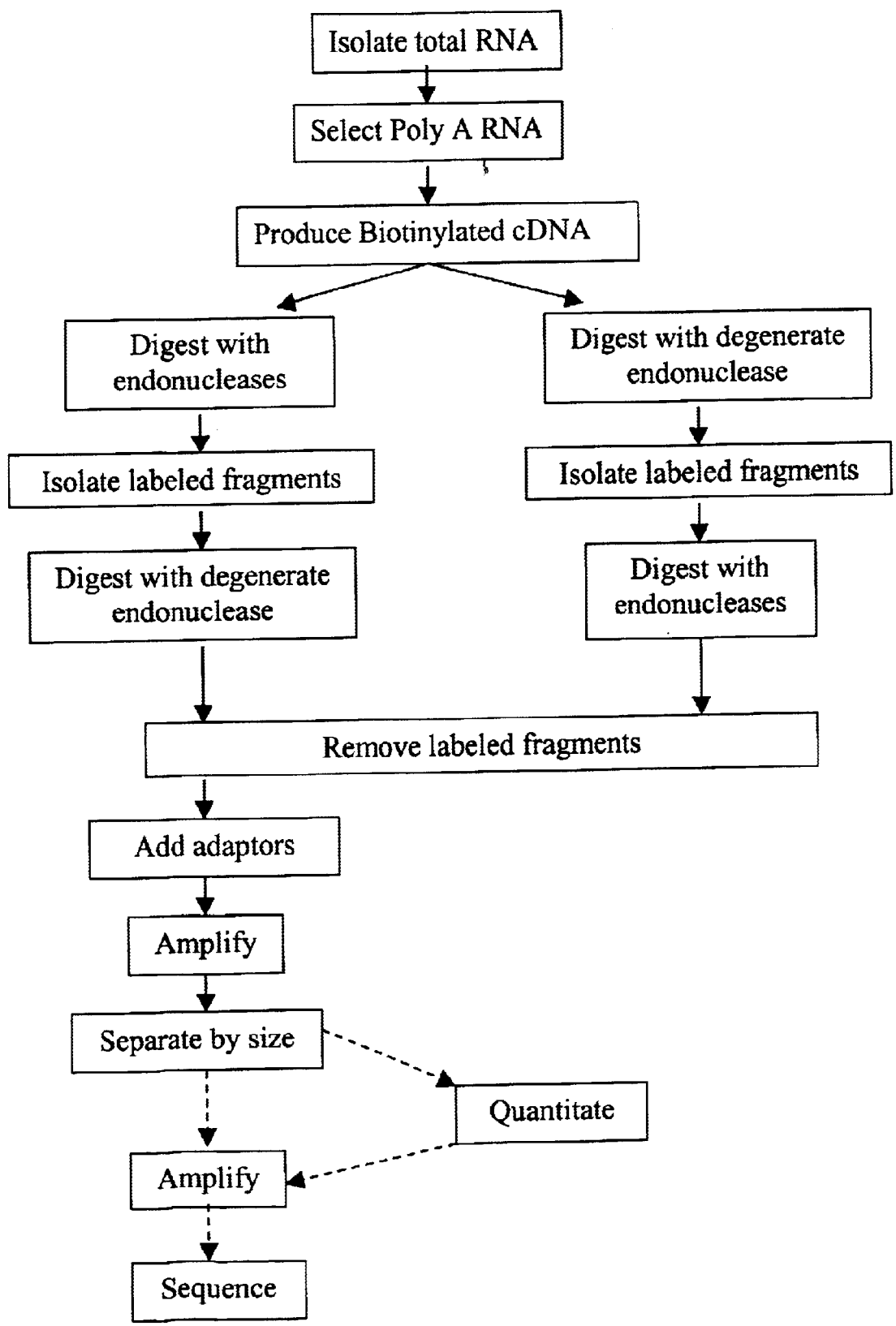
FIG. 2 shows a schematic representation of one embodiment of the disclosed method using two digestions where the digestion products are combined prior to adapter ligation. Arrows with broken lines indicate optional steps.
Figure 3:
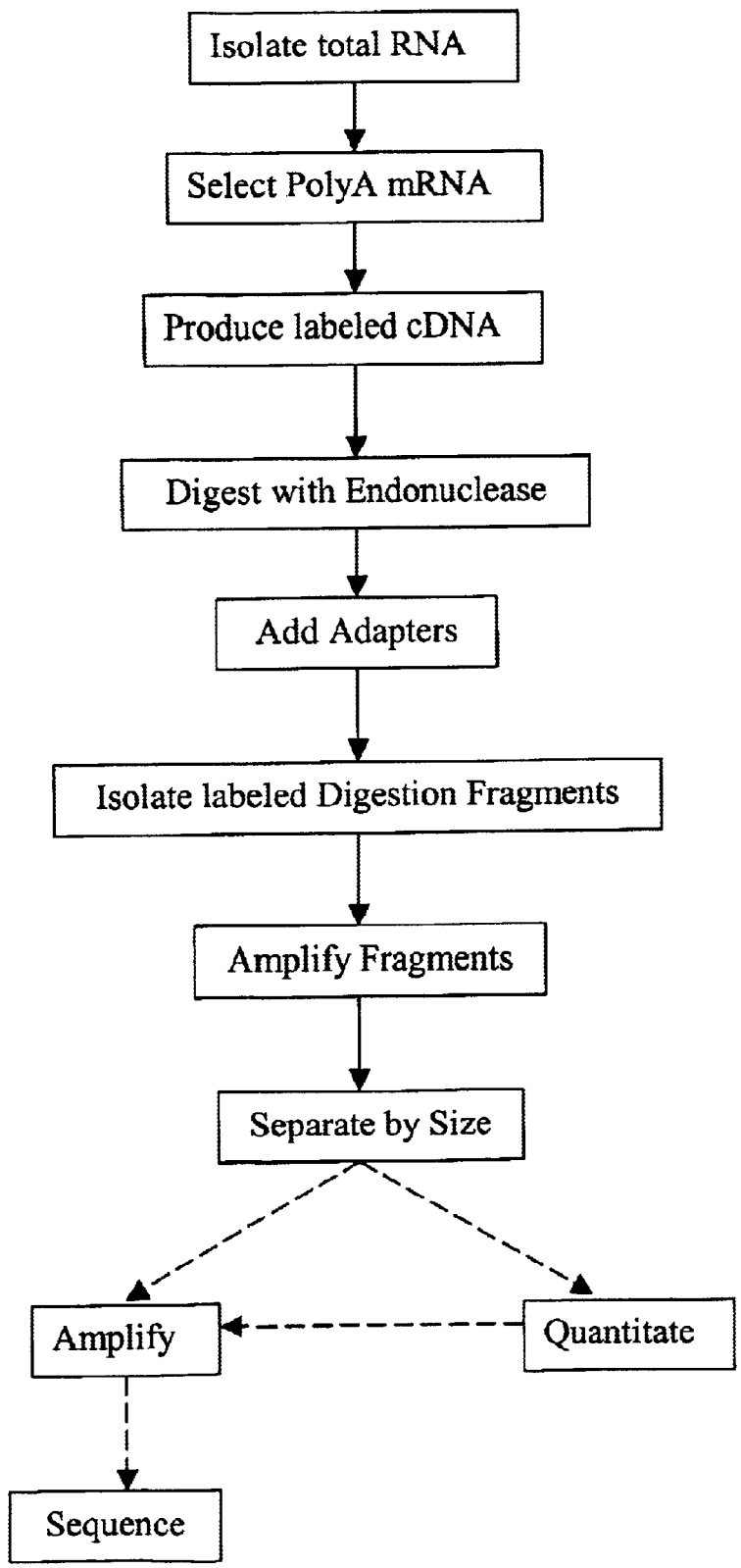
FIG. 3 shows a schematic of one embodiment of the disclosed method using a single digestion. Arrows with broken lines indicate optional steps.

Following the second digestion, selective double-stranded adapters are ligated to the fragments generated. At this point the portions can be combined or they can be kept separate (Compare FIGS. 1 and 2). As will be apparent to one skilled in the art, the number of adapters necessary to bind to each population of fragments generated will vary with the type and number of restriction endonucelases used. For example, if a total of six sequence specific endonucleases are used six different selective adapters will be needed. In addition, the number of adapters necessary for the enzymes having a degenerate recognition sequence will vary with the number of degenerate bases and the extent of degeneracy. The number of adapters necessary can also vary with the length of the single stranded region generated by endonuclease digestion. By way of illustration, a total of 64 ($4^3$) different adapters could be used with an endonuclease that generates a single stranded region having three fully degenerate bases. Thus, in Example 1, a total of 384 (64×6) adaptor combinations are possible. It will be apparent to those skilled in the art, that depending on the composition of the starting material, binding sites may not be present for all possible selective adapters. Likewise, it is not necessary that all possible selective adapters be used.

In one embodiment, the specific adapters comprise sequences that are common to all adapters of a particular group in addition to the sequences specific for particular digestion products. Preferably these common sequences have a low degree of homology to known sequences for the organism from which the library is constructed. For example, all selective adapters for use with sequence specific endonucleases can contain a common sequence, while all selective adapters for use with endonucleases having a degenerate recognition site can share another common sequence. These common sequences are often from 5 to 100 bases long, ordinarily from 8 to 25 bases long, and more commonly from 9 to 18 bases long. For example, in the case where the sequence specific endonuclease(s) used produces digestion products with a four-base overhang, adapters having the sequence:

```
5' gctgctagtgtccgatgt 3'     (SEQ ID NO.:1)

3' gatcacaggctacannnn 5'     (SEQ ID NO.:2)
``` where n represents bases specific for the endonuclease used. In one embodiment, selective adapters for use with endonucleases having degenerate recognition sequences are designed with different length single stranded overhangs on the 3' and 5' ends to prevent self ligation. Selective adapters can be produced by well-known methods for the production of oligonucleotides (Gait, *Oligonucletide Synthesis: A Practical Approach*, IRL Press, 1984; Beaucage and Caruthers, *Tetrahedron Letts*, 22:1859–1862, 1981; Beaucage and Iyer, *Tetrahedron*, 48:2223–2311, 1992; Caruthers et al., *Nucleic Acids Res. Symp. Ser.*, 7:215–223, 1980) or obtained from commercial sources. Double stranded adapters are ordinary produced one strand at a time. Annealing of the two strands can be accomplished prior to addition to the digested cDNA fragments or alternatively, each strand of the adapter can be added and the formation of a double stranded adapter allowed to proceed simultaneously with the annealing to the digested cDNA fragments.

In designing double-stranded adapters it is desirable that the upper and lower strands do not form stable secondary structures such as hairpins that will prevent annealing of the complementary sequences. Similarly, any singled stranded areas in the double-stranded adapters should not contain palindromic sequences in order to avoid adapter self-annealing. Additionally it is desirable that the adapter sequences not contain restriction enzyme recognition sites. Likewise, it is desirable that the ligation of the adapter to the fragment not create a restriction enzyme recognition site.

Ligation is accomplished by combining the digestion products with the selective adapters, and an appropriate DNA ligase in a suitable buffer solution. Any suitable DNA ligase may be used in practicing the invention. In one embodiment, T4 DNA ligase is used. The use of a DNA ligase serves the purpose of imparting a high degree of specificity and consistency, thus maintaining concordance between the actual profile of the starting nucleic acids and the ultimate library produced. Ligases are highly specific in their hybridization requirement. For example, even a single base mismatch near the ligation site will prevent ligation from occurring (see e.g. U.S. Pat. Nos. 5,366,877 and 5,093,245). The requirement by DNA ligase of perfectly complementary strands of annealed DNA distinguishes the method disclosed herein from other methods that rely on the extension of partially matched or mismatched primers and the resultant non-specific generation of fragments by DNA polymerases in the polymerase chain reaction (PCR). In the present method, PCR is used only for amplification purposes, and not for fractionating the nucleic acids into various pools. Moreover, the use of perfectly matched primers avoids the problem of non-specific priming and amplification often observed when degenerate primers are used in PCR. In addition, the use of a limited number of perfectly matched primers permits the use of higher annealing temperatures during PCR, which significantly enhances specificity and thus results in a library that accurately reflects the composition of the starting material.

Successfully ligated DNA fragments are then amplified. Any method of amplification can be used including PCR (U.S. Pat. Nos. 4,965,188, 4,800,159, 4,683,202, 4,683, 195), ligase chain reaction (Wu and Wallace, *Genomics*, 4:560–569, 1989; Landegren et al., *Science*, 241:1077–1080, 1988), transcription amplification (Kwoh et al. *Proc. Natl. Acad. Sci. USA*, 86:1173–1177, 1989), self-sustained sequenced replication (Guatelli et al., *Proc. Natl. Acad. Sci. USA*, 87:1874–1878, 1990) and nucleic acid based sequence amplification (NASBA). In one embodiment, amplification is accomplished by PCR using highly stringent conditions. The primers used are designed to make use of the regions of common sequence in the adapters. The use of the common sequence allows for the use of uniform, highly stringent conditions during amplification. In one embodiment, the primers contain detectable markers. In another embodiment, a detectable label is incorporated into the amplification product by the use of labeled dNTPs. Any detectable label that may coupled to a nucleic acid or nucleotide can be used. Non-limiting examples of suitable labels can be found Table 1.

As is well known in the art, the exact sequence of the primers used and so the conditions for conducting the amplification reactions will vary with the particular endonucleases used. Methods for primer design and optimization of PCR conditions can be found in standard molecular biology texts such as Ausubel et al., eds, *Short Protocols in Molecular Biology*, $3^{rd}$ ed, Wiley, 1995 and Innis et al., eds, *PCR Protocols*, Academic Press, 1990. More specific guidance can be found in the examples provided herein.

The amplification products are then fractionated on the basis of size and the individual fractions collected. As used herein, size can refer to the length and/or mass of the fragment. The use of thin polyacrylamide gel, such as that used for sequencing, is ideal for high resolution of DNA fragments differing in length by only a single nucleotide. Any alternative means for separation and isolation of DNA fragments by length or mass, preferably with high resolution, can be used. For example, such means include, among other possible methods, column chromatography, high pressure liquid chromatography (HPLC) or physical means such as mass spectroscopy. It is also possible to use unlabeled primers in PCR combined with alternative sensitive means of detecting the separated DNA fragments. For example, silver staining of polyacrylamide gels can be used to reveal fragments (Bassam et al., *Anal. Biochem.* 196: 80–83, 1991). Another sensitive means of detecting DNA fragments is the use of DNA intercalating dyes such as ethidium bromide, propidium iodide, acridine orange, Hoechst 33258 and Hoechst 33342. The method of detection and analysis of the pattern can be integrated and automated. In one embodiment, a fraction collection method, which is able to collect every individual band as a distinct fraction, is used for the purpose. For instance, a high resolution capillary electrophoresis coupled with a fraction collector can be used to collect fractions with interval small enough (such as 10 seconds/fraction) to ensure only one band in each fraction. For a lower throughput, the individual bands can also be excised from a slab gel and the DNA eluted.

Once separated, the quantity of each fragment present can be determined. Any method capable of quantitating the amount of each fragment present can be used such as fluorography, densitometry and photometry. In one example, an image of the gel used to separate the fragments and showing the bands associated with the fragment is captured and analyzed. Any medium capable of capturing an image can be used, for example chemical based method and electronic methods. Once captured, the bands can be analyzed by methods known in the art to determine the amount of each fragment present.

In an alternative embodiment, a non-redundant library is constructed using only a single endonuclease digestion step. In this embodiment, double-stranded cDNA is obtained from RNA by reverse transcription preferably using the labeled primer 5' $Seq_1(T)_x VN$. The resulting double-stranded cDNA is then subjected to a single digestion with at least one restriction endonuclease that preferably generates a single stranded overhang or protruding end. Sequence-specific endonucleases, endonucleases with degenerate recognition sequences, or combinations of both types can be used. In one embodiment, endonucleases with degenerate recognition sequences that generate single-stranded overhangs containing degenerate bases are used. The digestion products are then ligated to a series of adapters that contain sequences complementary to the overhangs produced as well as a sequence common to the adapters. As discussed previously, the high degree of specificity required for ligation ensures that only perfectly matched adapters are ligated.

Following ligation, the 3' ends of the fragments are isolated using the label contained in 5' $Seq_1(T)_x VN$ primer. Isolation of the 3' fragments can be achieved by any suitable method including capture on a solid substrate as described herein. Successfully ligated cDNA fragments are amplified, preferably by PCR, under uniform and highly stringent conditions, using 5' primers designed from the adapter sequences and a common 3' primer derived from the $Seq_1$ region of the primer used for reverse transcription. The 3' end of the 5' PCR primer can optionally contain one or two degenerate bases to allow for further fractionation. Following amplification, the amplification products can be fractionated on the basis of size as previously described.

Whether produced using a single or double digestion, each individually isolated fragment representing a distinct RNA species is PCR amplified using primers that incorporate universal primer sequences (such as M13 forward and reverse primers). Once the universal primer sequences are incorporated at the ends of the fragments, all the PCR amplified fragments can be directly sequenced using a single universal primer without cloning. This eliminates the intermittent step of cloning and thereby introduces simplicity, speed and cost-saving measures. Any method for direct sequencing can be used including dideoxy sequencing, chemical sequencing, pyrosequencing and variants thereof.

Methods of direct sequencing are well known in the art and can be found in standard molecular biology texts such as Ausubel et al., eds., *Short Protocols in Molecular Biology*, 3$^{rd}$ ed., Wiley, 1995 and Sambrook et al., *Molecular Cloning*, 2$^{nd}$ ed., Cold Spring Laboratory Press, 1989, Chap. 13.

Since each fragment in a library prepared by the described methods corresponds to a single species of RNA, the resultant library is devoid of redundant clones or has only minimal redundancy. As mentioned earlier, all the existing methods of making expression libraries suffer from a common disadvantage of inherent redundancy, which considerably increases the number of fragments to be sequenced in order to achieve genome wide coverage. It is estimated that there are 15,000–20,000 distinct transcripts expressed in a given cell type. A conventional library of approximately 500,000 fragments needs to be sequenced to represent these transcripts. Moreover, transcripts expressed at low level may still remain undetected notwithstanding sequencing efforts on such large scale. In contrast, the method of the present invention generates a library with little or no redundancy (a non-redundant library). Accordingly, each transcript is represented by a unique fragment in the library. As a consequence, the number of fragments to be sequenced for a genome wide coverage of transcripts is reduced to about 25,000 to 50,000. This translates into increased speed and cost effectiveness. The method disclosed also offers additional advantages, for example, elimination of intermediate step(s) of cloning fragments and representation of hard-to-find transcripts. The fragments generated and sequenced can be either kept in the form of PCR products or cloned into a suitable vector and maintained like a conventional library.

The methods described herein provide a powerful tool to construct a polynucleotide library without redundancy or with minimal redundancy. They also provide direct sequencing of fragments generated, without the intermittent step of cloning. The methods overcome an important shortcoming of the existing methods of preparing libraries, i.e. redundant occurrence of clones of highly expressed genes and under-representation of clones corresponding to low level transcripts. Therefore, the present methods save considerable time, effort and money in preparing the library. A non-redundant library prepared according to the instant methods provides a source of information about all the expressed genes in a given cell type. The non-redundant library also provides a valuable set of highly specific cDNA tags that can be used to monitor the expression of corresponding genes in any cell type. The tags generated by the disclosed methods are considerably longer than those obtained with other methods such as SAGE (serial analysis of gene expression, Yamamoto et al., *J. Immunol. Meth.*, 250:45–66, 2001; U.S. Pat. Nos. 5,695,937 and 5,866,330). Higher length, coupled with non-redundant nature, makes these tags particularly suitable for comprehensive genome wide gene expression analysis. For example, PCR amplified fragments produced by the methods described herein, or oligonucleotides derived or designed from them, can be used as tags for building microarrays. A microarray format based on such tags provides a highly versatile tool for a wide range of applications, such as expression profiling. Methods for the production and use of microarrays are well known in the art and can be found, for example in *Nature Genetics*, Suppl. 1, Vol. 21, January, 1999.

Thus one embodiment provides a method for detecting a change in RNA expression pattern associated with an internal or external factor. Using the methods provided herein, a cDNA library is constructed from a first cell or tissue that has been exposed to the internal or external factor of interest and the pattern of RNA expression determined. The pattern of RNA expression can be based on the present or absence of certain cDNA fragments or quantitative determination of the different cDNA molecules present in the library. The cell or tissue can be of any type, for example from an animal or plant. Factors can be environmental factors, disease causing organisms, chemicals, drugs, hormones, growth factors, and the like. A second cDNA library is then constructed from a second cell or tissue, preferably from the same species and/or from the same cell or tissue type, that has not been exposed to the internal or external factor of interest and the pattern of RNA expression determined. The RNA expression patterns between the first and second cells or tissues is then compared and any differences noted. In one embodiment, data representing the RNA expression pattern of the second cell or tissue is stored on a computer readable medium so that the RNA expression pattern from the first cell or tissue type can be compared to the stored RNA expression pattern from the second cell or tissue type.

Expression profiling can often reveal an important physiological pathway. Genes showing differential expression may provide useful targets for screening therapeutic compounds or may provide a basis of a diagnostic test. Temporal changes detected using non-redundant sequence tag-based microarrays described herein can also be useful in prognosis. Moreover, the methods as outlined herein can also be used for monitoring quantitative changes in gene expression in a given cell type under different conditions. For example, a change in the pattern of gene expression during various stages of growth, development or differentiation can be studied. Changes in gene expression during various phases of cell cycle in a synchronized population of cells can also be conveniently examined. A profile of gene expression in a given cell type in response to the treatment with growth factor or cytokine can be established, and this may help elucidate mechanisms of signal transduction. Temporal changes in gene expression that accompany different stages of signal transduction can be investigated using the approach disclosed herein. Genes that play an important role in cell transformation can be isolated and characterized. Such genes may provide therapeutic targets for prevention or treatment of cancer. Furthermore, these genes may also provide diagnostic or prognostic means. The methods are also applicable to the assessment of effect of drugs on gene expression wherein cells treated with or without a drug are subjected to the method described herein and comparison of the gene expression profile reveals the effect of drug on global gene expression.

The methods provided can also be used to determine the physiological or developmental state of a cell or tissue. In this embodiment, a RNA expression is determined in a first cell or tissue of a known physiological or developmental state by constructing a cDNA library using the instant methods and the pattern of RNA expression determined. The tissues or cells can be obtained from any source, for example plants or animals. A second cDNA library is then constructed from a second cell or tissue, preferably from the same species and/or from the same cell or tissue type, that is of an unknown developmental or physiological state and the pattern of RNA expression determined. The RNA expression patterns between the first and second cells or tissues is then compared and any differences noted. In one embodiment, data representing the RNA expression pattern of the first cell or tissue is stored on a computer readable medium so that the RNA expression pattern from the second cell or tissue type can be compared to the stored RNA expression pattern from the first cell or tissue type.

The methods disclosed herein are also useful for diagnosing a disease, condition, disorder or predisposition associated with a change in RNA expression patterns. As used herein, the term "predisposition" refers to the likelihood that an individual subject will develop a particular disease, condition or disorder. For example, a subject with an increased predisposition will be more likely than average to develop a disease, condition or disorder, while a subject with a decreased predisposition will be less likely than average to develop a disease, condition or disorder. The disease, condition, disorder, or predisposition may be genetic or may be due to a microorganism. In this embodiment, the pattern of RNA expression is determined by constructing a cDNA library using the present methods from a first cell or tissue know to have the disease, condition, disorder or predisposition and the pattern of RNA expression determined based on the cDNAs present in the library. The pattern of RNA expression is then determined in a second cell or tissue from a test subject, preferably of the same species and/or from the same cell or tissue type, using the methods described herein and the patterns of RNA expression compared. In one embodiment, data representing the RNA expression pattern of the first cell or tissue is stored on a computer readable medium so that the RNA expression pattern from the second cell or tissue type can be compared to the stored RNA expression pattern from the first cell or tissue type.

Comparison of the gene expression profiles between normal and diseased tissues can often yield valuable information about the genes whose activities are up-regulated or down-regulated during the course of pathogenesis. Some of the observed changes in gene expression may be causally related to the pathogenesis or may be of diagnostic value.

For example, a number of changes taking place at the genomic DNA level in cancer such as chromosomal translocation, gene amplification, loss of heterozygosity for an allele etc are reflected in changes in gene expression. Consequently, these changes can be monitored using the present method or unique sequence tags prepared by the present method. Such unique or non-redundant tags can be used to construct a microarray. For example, a number of specific chromosomal translocations involving and leading to activation of cellular proto-oncogenes have been reported in cancer cells. Similarly, a number of proto-oncogenes are amplified in cancer cells. As a result, the expression of some of these proto-oncogenes is increased. A microarray based approach using a panel of non-redundant tags derived from cellular proto-oncogenes can be used to monitor the expression of a wide variety of proto-oncogenes in parallel.

Furthermore, an analysis carried out as per the disclosed method may also aid in the diagnosis of "loss of heterozygosity" (LOH) mutations, i.e. mutation of the second (normal) allele of a tumor suppressor gene that often results in the emergence of cancer cells. The tumor suppressor genes (e.g. retinoblastoma susceptibility gene, p53, DCC, APC etc) are recessive genes, unlike proto-oncogenes which are dominant genes. Therefore, inheritance of a single mutant allele (heterozygous state) of these genes does not lead to cellular transformation, but only predisposes an individual to cancer. Mutation of the second normal allele of a tumor suppressor gene in the same cell (loss of heterozygosity), however, leads to transformation, immortalization and finally results in a tumor or cancer. Mutation of certain tumor suppressor genes (e.g. RB in retinoblastoma tumors) increases their expression, whereas that of others (e.g. p53 in various cancers) leads to decreased expression.

The methods disclosed herein can be used for the diagnosis of a variety of cancers such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

The instant methods are also applicable to plants for various agricultural uses. For example, non-redundant libraries and tags prepared from a plant can be used to examine the effect of chemical compounds on plants and agriculturally related organisms, and further to establish the mode of action of such compounds. A microarray based on non-redundant fragments, for example, non-redundant EST fragments, can be used to study expression profiles of genes from plants or fungi, treated with or without herbicide or fungicide respectively, and can be compared to identify genes whose expression level is altered in response to the treatment. The temporal changes in the expression of these genes can yield valuable information regarding the mode of action of the compounds. Further optimization of the lead compounds can be performed using the established profile of gene expression.

The methods can also be used for the identification of gene(s) whose expression is associated with a specific phenotype. For example, comparison of non-redundant EST libraries prepared from a pool of high oil and low oil corns may help identify the genes which may be responsible, directly or indirectly, for the observed phenotypic differences. Furthermore, the method can be used to identify compounds that can enhance or suppress a specific phenotype by following changes in the established profile in response to the treatment. For example, the rubber production of a rubber tree can be induced by the repeated cutting of the bark to collect rubber. The genes related to rubber synthesis can be identified and characterized through the comparison of gene expression profile in dormant and active rubber production trees.

Another use of the present methodologies in the agricultural field is the identification of genes controlling quantitative traits. Many agronomically important traits such as yield, height, stalk stability, and early vigor are quantitative traits. The method described herein can be used to study the global quantitative gene expression changes associated with those traits. The genes thus identified can then be used as markers for selection of the favored traits.

Additionally, the disclosed methods can be used to identify the gene(s) responsible for a mutant phenotype by comparing the gene expression profiles of mutant and wild-type plants. Similarly, the disclosed methods can be used to identify plant genes responsible for resistance or susceptibility to various physical, chemical or biological agents such as drought, salinity, pathogens (bacterial, viral, fungal, or insects), etc. A gene thus identified can be used as a transgene or to create knock-outs to modify the response of plants to these agents. This is a very important application as large amounts of crops are destroyed or affected adversely, for example in yield or quality, every year as a result of these agents.

Additionally, the methods described herein can be applied to non-model species of which little sequence information is known, for example medical herbs, to quickly sample for genes unique to the species and to identify important metabolic pathways.

TABLE 1

| Fluorochrome | Supplier* | Absorption Maximum | Emission Maximum |
|---|---|---|---|
| Bodipy | Molecular Probes | 493 | 503 |
| 493/503 Cy2 | BDS | 489 | 505 |
| Bodipy FL | Molecular Probes | 508 | 516 |
| FTC | Molecular Probes | 494 | 518 |
| FluorX | BDS | 494 | 520 |
| FAM | Perkin-Elmer | 495 | 535 |
| Carboxy-rhodamine | Molecular Probes | 519 | 543 |
| EITC | Molecular Probes | 522 | 543 |
| Bodipy 530/550 | Molecular Probes | 530 | 550 |
| JOE | Perkin-Elmer | 525 | 557 |
| HEX | Perkin-Elmer | 529 | 560 |
| Bodipy 542/563 | Molecular Probes | 542 | 563 |
| Cy3 | BDS | 552 | 565 |
| TRITC | Molecular Probes | 547 | 572 |
| LRB | Molecular Probes | 556 | 576 |
| Bodipy LMR | Molecular Probes | 545 | 577 |
| Tamra | Perkin-Elmer | 552 | 580 |
| Bodipy 576/589 | Molecular Probes | 576 | 589 |
| Bodipy 581/591 | Molecular Probes | 581 | 591 |
| Cy3.5 | BDS | 581 | 596 |
| XRITC | Molecular Probes | 70 | 596 |
| ROX | Perkin-Elmer | 550 | 610 |
| Texas Red | Molecular Probes | 589 | 615 |
| Bodipy TR | Molecular Probes | 596 | 625 |
| Cy5 | BDS | 650 | 667 |
| Cy5.5 | BDS | 678 | 703 |
| DdCy5 | Beckman | 680 | 710 |
| Cy7 | BDS | 443 | 767 |
| DbCy7 | Beckman | 790 | 820 |

*The suppliers listed are Molecular Probes (Eugene, OR), Biological Detection Systems ("BDS") (Pittsburgh, PA) and Perkin-Elmer (Norwalk, CT).

EXAMPLES

The following examples are intended to provide illustrations of the application of the present invention. The following examples are not intended to completely define or otherwise limit the scope of the invention.

Example 1

Construction of Non-Redundant Library Using Two Digestions 1.1 Total RNA Isolation Three grams of frozen plant tissue were added to liquid nitrogen in a mortar and pestle on dry ice. Care was taken to prevent thawing of the tissue during weighing. The tissue was ground, under liquid nitrogen, to a fine powder and the powder transferred with a small amount of liquid nitrogen to a disposable polypropylene 50 ml test tube. Immediately after evaporation of the liquid nitrogen, 30 ml (10 ml/g tissue) of RNAwiz (Ambion, Austin, Tex., cat #9736) was added and thoroughly mixed with the powder, taking care not let the powder thaw prior to mixing. The powder RNAwiz mixture was then homogenized at 5,000–30,000 rpm using Tissue Tearor (model 985370, Biospec Products, Inc.) for not more than 2 minutes and incubated at room temperature for another 5 minutes. Following homogenization, 6 ml (0.2 vol of RNAwiz) of chloroform was added, the tube vigorously shaken by hand for about 20 seconds, and the mixture incubated at room temperature for 10 minutes.

Next, the mixture was centrifuged at 4° C., 12,000×g for 15 minutes and the aqueous phase transferred to a new 50 ml tube taking care not to disturb the semi-solid interface. In cases where the interface was heavy, a second chloroform extraction was performed. For the second extraction, the volume of the aqueous phase (V) was determined and an equal amount of RNAwiz added followed by mixing and a 5 minute incubation at room temperature. Next, 0.2 V of chloroform was added, the mixture hand shaken for about 20 seconds, and then incubated at room temperature for 5 minutes. The mixture was then centrifuged as described above, the aqueous layer carefully transferred to a new 50 ml tube, and the process repeated.

Following the chloroform extraction, 15 ml (0.5 vol of starting RNAwiz) of nuclease-free water was added, mixed well, and the resulting mixture divided into two new 50 ml tubes. Fifteen ml (0.5 vol of starting RNAwiz) of isopropanol was added to each tube, mixed, and the tube incubated for 10 minutes at room temperature. The tubes were then centrifuged at 4° C., 12,000×g for 15 minutes; the supernatant discarded; and the pellet washed with approximately 15 ml of 70% ethanol (−20° C.) by gentle vortexing. The RNA was re-pelleted by centrifugation at 4° C., 12,000×g for 5 minutes, and the washing procedure repeated. Following the second wash, the ethanol was removed and the pellet allowed to air dry for about 10 minutes to remove residual ethanol. After drying, the pellets were combined and re-suspended in 0.5 ml of nuclease-free water. If the re-suspended RNA solution was not completely clear, it was centrifuged at 4° C., 12,000×g for 15 minutes, the supernatant retained, and the gelatinous pellet of polysaccharides discarded.

To eliminate contaminating genomic DNA from the sample, an acid-phenol:chloroform extraction or DNase digestion was performed. For the extraction, an equal volume of acid-phenol:chloroform (Ambion, Austin, Tex., cat. # 9720) was added, the mixture vigorously shaken by hand, the tube centrifuged at room temperature, 14,000×g for 5 minutes, and the aqueous phase transferred to a new tube. To the aqueous phase was added 0.5 vol of 7.5M lithium chloride (final conc. 2.5M), the solutions mixed and the mixture incubated at −20° C. for 30 minutes to overnight. Following incubation, the mixture was centrifuged at 4° C., 14,000 rpm for 20 minutes and the pellet washed twice by vortexing with −20° C., 70% ethanol followed by centrifugation. Following the second centrifugation, the supernatant was removed and the residual ethanol allowed to evaporate for 5–10 minutes. Following drying, the pellet was re-suspended in 0.2 ml nuclease-free water.

For DNase digestion, approximately 50 μl of RNA solution (about 1 μg/μl) was mixed with 6.5 μl (1/10 final vol.) of 10×RNase-free DNase buffer (Invitrogen, Carlsbad, Calif.), 5.0 μl (0.1 μ/μg RNA) of RNase-free DNase (1 μ/μl) and 3.5 μl of nuclease free water and incubated at 37° C. for 30 minutes. Following incubation, an equal volume of phenol:chloroform:isopropanol (25:24:1) was added; the tube vigorously shaken by hand; centrifuged at room temperature, 14,000×g for 5 minutes; and the aqueous phase transferred to a new tube. To the aqueous phase was then added 1/10 volume of 3M sodium acetate (pH 5.5) and 2.5 volumes of absolute ethanol (−20° C.) and the mixture incubated overnight at −20° C. Following the incubation, the mixture was centrifuged at 4° C., 14,000 rpm for 30 minutes; the supernatant removed; the pellet washed twice with 1 ml of 70% ethanol at −20° C.; the pellet air dried for 5–10 minutes; and the pellet re-suspended in 0.1–0.2 ml of nuclease-free water. Purity and concentration of the RNA can be determined by optical density at 260, 280 and 230 nm. A sample of the RNA can also be check for degradation by formaldehyde gel electrophoresis.

1.2 Poly(A)$^+$ RNA Selection

Poly(A)$^+$ RNA was selected using the Oligotex mRNA kit (Qiagen) following the manufacturer's instructions. RNA was concentrated by addition of 1/10 volume of 3M sodium acetate (pH 5.5), 1 $\mu$l glycogen (5 mg/ml) and 2.5 volumes of absolute ethanol (−20° C.) followed by an overnight incubation. Following incubation, the mixture was centrifuged at 4° C., 14,000 rpm for 40 minutes and the supernatant carefully removed. The pellet was then wash with 75% ethanol (−20° C.), centrifuged as described for 30 minutes, and the supernatant carefully removed. The pellet was air dried and the poly(A)$^+$ RNA resuspended in a small volume of nuclease-free water to an estimated concentration of greater than 0.25 $\mu$g/$\mu$l. Actual concentration was determined by optical density at 260 nm. In addition, a sample of about 0.5 $\mu$g was analyzed by formaldehyde gel electrophoresis to check for degradation.

1.3 Biotinylated cDNA Synthesis

One $\mu$l of 5'-biotinylated oligo(dT)$_{18}$ primer (1 $\mu$g/$\mu$l) (L-(dT)$_{18}$NV) was combined with 2.5–3.0 $\mu$g of poly(A)$^+$ RNA into a test tube and DEPC-treated water added to bring the final volume to 11 $\mu$l. The mixture was heated in a dry bath to 70° C. for 15 minutes and then quickly chilled on ice for about 5 minutes. After chilling, the contents of the tube were collected by a brief centrifugation, followed by the addition of 4 $\mu$l first strand buffer (SuperScript Choice Kit, Life Technologies, cat. #11928-017), 2 $\mu$l DTT (0.1M), and 1 $\mu$l dNTP (10 mM each) for a total volume of 18 $\mu$l. The reagents were mixed by tapping, collected by brief centrifugation, and the tube incubated in a dry bath for 2 minutes at 37° C. to equilibrate the temperature. Next, 2 $\mu$l of Superscript II reverse transcriptase (200 units/$\mu$l, SuperScript Choice Kit, Life Technologies, cat. #11928-017) were added, the contents of the tube mixed by gentle pipeting, and the mixture incubated at 37° C. for 1 hour.

Following incubation, the contents of the tube were collected by brief centrifugation, the tube placed on ice, and the following reagents added in the order of 91 $\mu$l DEPC-treated water, 30 $\mu$l 5×Second Strand Buffer (SuperScript Choice Kit, Life Technologies, cat. #11928-017), 3 $\mu$l dNTP mix (10 mM each), 1 $\mu$l E. coli DNA ligase (10 units/$\mu$l), 4 $\mu$l E. coli DNA polymerase (10 units/$\mu$l), and 1 $\mu$l E. coli RNase H (2 units/$\mu$l) for a total volume of 150 $\mu$l. The contents of the tube were mixed by gentle pipeting and the mixture incubated at 16° C. for 2 hours.

Following the incubation, the tube was placed on ice and 10 $\mu$l of EDTA added with gentle mixing. Next, 160 $\mu$l of phenol:chloroform:isoamyl alcohol (25:24:1) was added and the mixture vortexed until the two phases mixed. The tube was then centrifuged at room temperature, 14,000×g for 5 minutes and 150 $\mu$l of the aqueous phase transferred to a new tube. To this was added, 75 $\mu$l (0.5 vol.) of 7.5M ammonium acetate, 1 $\mu$l of glycogen (5 mg/ml), and 563 $\mu$l (2.5 vol.) of absolute ethanol (−20° C.). The contents were mixed, the tube immediately centrifuged at room temperature, 14,000 rpm for 30 minutes, and the supernatant carefully and completely removed. The pellet was then rinsed with 1.0 ml of 70% ethanol (−20° C.), centrifuged at room temperature, 14,000 rpm for 15 minutes, the supernatant removed, and the pellet air dried in a 37° C. dry bath for 5–10 minutes. The pellet was then dissolved in low TE (1 mM Tris-HCl, pH 7.5 and 0.1 mM EDTA) to a concentration of about 50 ng/$\mu$l.

1.4 First Restriction Enzyme Digestion

The biotinylated cDNA was divided into two portions. Portion I was digested with six, 6-cutter restriction endonucleases stimultaneously, while portion II, was digested with Bsl I (CCNN,NNN'NNGG). The portion I test tube was placed on ice and 80 $\mu$l of 10×NEBuffer 2 (New England Biolabs, Beverly, Mass.), 80 $\mu$l 10×BSA (1 mg/ml), 560 $\mu$l nuclease-free water, 50 $\mu$l biotinylated cDNA (~2500 ng), 7.5 $\mu$l ApaL I (10 U/$\mu$l), 3.75 $\mu$l BamH I (20 U/$\mu$l), 3.75 $\mu$l EcoR I (20 U/$\mu$l), 3.75 $\mu$l Hind III (20 U/$\mu$l), 7.5 $\mu$l Nco I (10 U/$\mu$l), and 3.75 $\mu$l Xho I (20 U/$\mu$l) were added for a final volume of 800 $\mu$l. The reagents were gently mixed, the contents collected by brief centrifugation and the tube incubated for 1.5 to 2 hours at 37° C.

The portion II test tube was placed on ice and 80 $\mu$l 10×NEBuffer 3 (New England Biolabs, Beverly, Mass.), 80 $\mu$l 10×BSA (1 mg/ml), 575 $\mu$l nuclease-free water, 50 $\mu$l biotinylated-cDNA (2000–2500 ng), and 15 $\mu$l Bsl I (10 U/$\mu$l) were added for a final volume of 800 $\mu$l. The contents of the tube were mixed, collected by brief centrifugation and the mixture incubated for 1.5 to 2 hours at 55° C.

1.5. Biotinylated 3'-End Fragment Capture

Just prior to use, 100 $\mu$l of streptavidin-coated beads (Dynabeads, M-280, Dynal Biotech, Lake Success, N.Y., cat. # 112.05) were added to each of four, 1.5 ml tubes labeled I-1, I-2, II-1 and II-2. The beads were separated from the liquid by setting the tubes on a magnetic stand (Dynal, MPC-E) for 1–2 minutes and the liquid removed. The beads were then washed twice with 800 $\mu$l of 1×WB solution (1M NaCl, 5 mM Tris-HCl, pH 7.5, 0.5 mM EDTA, pH 8.0) to remove any free streptavidin. Washing was performed by slowly inverting the tube, centrifuging the tube for less than 1 second, placing the tube on the magnetic stand for 1–2 minutes, and removing the supernatant by pipeting. Once washed, the beads were used within 1 hour.

Four hundred $\mu$l of digested cDNA was placed in each of a second set of appropriately labeled tubes followed by 400 $\mu$l of 2×WB solution (2M NaCl, 10 mM Tris-HCl, pH 7.5, 1 mM EDTA, pH 8.0) and mixing. The 800 $\mu$l in each tube was then transferred to the correspondingly labeled tube containing the beads, mixed by slowing inverting the tubes, and then rotated for 1 hour at room temperature. The tubes were then placed on a magnetic stand for 3 minutes and the supernatant removed by pipeting. The beads where next washed four times with 0.8 ml 1×WB solution during which tubes I-1 and I-2 were combined as were tubes II-1 and II-2. The beads were next washed once with 0.8 ml of low TE buffer (1.0 mM Tris-HCl, pH 7.5, 0.1 mM EDTA) and once with 0.8 ml of 1×NEBuffer 3 for portion I and 0.8 ml of 1×NEBuffer 2 for portion II.

1.6. Second Restriction Enzyme Digestion and Non-redundant Fragment Release

In a tube on ice, 100 $\mu$l of 10×NEBuffer3, 100 $\mu$l of 10×BSA (1 mg/ml), 785 $\mu$l of nuclease-free water, and 15 $\mu$l of Bsl I (10 U/$\mu$l) were combined for a final volume of 1000 $\mu$l. This mixture was then added to the tube containing the portion I washed beads, the contents of the tube mixed by slowly inverting the tube, and the sealed tube rotated at 55° C. for 1.5–2 hours.

In another tube on ice, 100 µl of NEBuffer2, 100 µl 10×BSA (1 mg/ml), 770 µl of nuclease-free water, 7.5 µl of ApaL I (10 U/µl), 7.5 µl of NcoI (10 U/µl), 3.75 µl of BamH I (20 U/µl), 3.75 µl of EcoR I (20 U/µl), 3.75 µl of Hind III (20 U/µl), and 3.75 of Xho I (20 U/µl) were combined for a total volume of 1000 µl. This mixture was added to the tube containing the portion II washed beads, the contents mixed by inverting the tube, and the tube rotated at 37° C. for 1.5–2 hours.

Following digestion, the beads were separated from the supernatant containing the non-redundant fragments by placing the tubes on a magnetic stand for 3 minutes and transferring the supernatant from each of the portion I and portion II tubes to new 1.5 ml tubes. To remove any remaining beads, the tubes were again placed on a magnetic stand for 3 minutes and the clear supernatant for each portion removed and placed in new 1.5 ml tubes. If necessary, the volume of each tube was brought to 1000 µl by the addition of nuclease-free water.

1.7. Selective Adapter Ligation

Ligation reactions were conducted in 96-well PCR plates. The adapters used are shown in Table 2 Eight plates were used for a total of 768 wells. To each well, 2.5 µl of restriction enzyme digested cDNA produced as described above, 2.5 µl (0.125 pmol) of one of the restriction enzyme specific adapters for each of the six restriction enzymes used, and 0.015 µl (0.0625 pmol) of one of the 64 possible Bsl I adapters was sequentially added for a total volume of 7.5 µl. After each addition, the plates were briefly centrifuged at 2500 rpm to bring the contents to the bottom of the well and the contents mixed by gentle vortexing. The plates were then incubated at room temperature for at least 1.5 hours to allow for adapter binding. After the incubation, 2.5 µl (1.5 units) of T4 DNA ligase in ligase buffer mix (New England Biolabs, Beverly, Mass.) was added to each well for a final volume of 10 µl per well, the plates centrifuged to bring the contents to the bottom and the contents mixed by gentle vortexing.

The resulting contents of the wells is shown if Table 4. In Table 4, for each 96-well plate depicted, the numbers across the top indicate the plate column while the letters down the side indicate the plate rows. The heading for each column indicates the sequence specific endonuclease adapters of Table 1 used in wells of that column where ApaL I is AB18-ApaL I, BamH I is AB18-BamH I, EcoR I is AB18-EcoR I, Hind III is AB18-Hind III, Nco I is AB18-Nco I, and Xho I is AB18-Xho I. Within each well, the degenerate endonuclease adapter used is indicated by the three nucleotides given in bold in Table 2. For example AAA corresponds to adapter CD18-Bsl I-AAA in Table 2. The designation above columns 1–6 and 7–12 indicate the order in which the endonucleases were used on that sample. For example, 6RE→Bsl I indicates that fragments in those wells were produced by first digesting the cDNA with the mixture of six sequence-specific nucleotides followed by digestion with Bsl I, i.e. portion I of Example 1.

For each 96-well plate, wells in columns 1–6 contained portion I cDNA and wells in columns 7–12 contained portion II cDNA. For each 96-well plate, columns 1–6 contained different adapters specific for each of the six, 6-base cutter endonucleases used. This was repeated for columns 7–12. Each row contained a different Bsl I adapter so that all of the 64 possible adapters were present when all eight plates were combined (8 plates×8 rows/plate). After addition of the ligase, the plates were incubated at 16° C. for 2 hours.

TABLE 2

| ADAPTER | | SEQUENCE | |
|---|---|---|---|
| AB18-ApaL I | 5' | GCTGCTAGTGTCCGATGT 3' | (SEQ ID NO:3) |
| | 3' | GATCACAGGCTACAACGT 5' | (SEQ ID NO:4) |
| AB18-BamH I | 5' | GCTGCTAGTGTCCGATGT 3' | (SEQ ID NO:3) |
| | 3' | GATCACAGGCTACCTAG 5' | (SEQ ID NO:5) |
| AB18-EcoRI | 5' | GCTGCTAGTGTCCGATGT 3' | (SEQ ID NO:3) |
| | 3' | GATCACAGGCTACTTAA 5' | (SEQ ID NO:6) |
| AB-18 Hind III | 5' | GCTGCTAGTGTCCGATGT 3' | (SEQ ID NO:3) |
| | 3' | GATCACAGGCTACATCGA 5' | (SEQ ID NO:7) |
| AB18-Nco I | 5' | GCTGCTAGTGTCCGATGT 3' | (SEQ ID NO:3) |
| | 3' | GATCACAGGCTACGTAC 5' | (SEQ ID NO:8) |
| AB18-Xho I | 5' | GCTGCTAGTGTCCGATGT 3' | (SEQ ID NO:3) |
| | 3' | GATCACAGGCTACTCGA 5' | (SEQ ID NO:9) |
| CD18-Bsl I-AAA | 5' | GATCTCCTAGAGTCGTGAAAA 3' | (SEQ ID NO:10) |
| | 3' | NH$_2$-CTCAGCACT-Pi 5' | |
| CD18-Bsl I-AAG | 5' | GATCTCCTAGAGTCGTGAAAG 3' | (SEQ ID NO:11) |
| | 3' | NH$_2$-CTCAGCACT-Pi 5' | |
| CD18-Bsl I-AAC | 5' | GATCTCCTAGAGTCGTGAAAC 3' | (SEQ ID NO:12) |
| | 3' | NH$_2$-CTCAGCACT-Pi 5' | |
| CD18-Bsl I-AAT | 5' | GATCTCCTAGAGTCGTGAAAT 3' | (SEQ ID NO:13) |
| | 3' | NH$_2$-CTCAGCACT-Pi 5' | |
| CD18-Bsl I-AGA | 5' | GATCTCCTAGAGTCGTGAAGA 3' | (SEQ ID NO:14) |
| | 3' | NH$_2$-CTCAGCACT-Pi 5' | |
| CD18-Bsl I-AGG | 5' | GATCTCCTAGAGTCGTGAAGG 3' | (SEQ ID NO:15) |
| | 3' | NH$_2$-CTCAGCACT-Pi 5' | |
| CD18-Bsl I-AGC | 5' | GATCTCCTAGAGTCGTGAAGC 3' | (SEQ ID NO:16) |
| | 3' | NH$_2$-CTCAGCACT-Pi 5' | |
| CD18-Bsl I-AGT | 5' | GATCTCCTAGAGTCGTGAAGT 3' | (SEQ ID NO:17) |
| | 3' | NH$_2$CTCAGCACT-Pi 5' | |
| CD18-Bsl I-ACA | 5' | GATCTCCTAGAGTCGTGAACA 3' | (SEQ ID NO:18) |
| | 3' | NH$_2$CTCAGCACT-Pi 5' | |
| CD18-Bsl I-ACG | 5' | GATCTCCTAGAGTCGTGAACG 3' | (SEQ ID NO:19) |
| | 3' | NH$_2$CTCAGCACT-Pi 5' | |
| CD18-Bsl I-ACC | 5' | GATCTCCTAGAGTCGTGAACC 3' | (SEQ ID NO:20) |
| | 3' | NH$_2$CTCAGCACT-Pi 5' | |
| CD18-Bsl I-ACT | 5' | GATCTCCTAGAGTCGTGAACT 3' | (SEQ ID NO:21) |
| | 3' | NH$_2$CTCAGCACT-Pi 5' | |
| CD18-Bsl I-ATA | 5' | GATCTCCTAGAGTCGTGAATA 3' | (SEQ ID NO:22) |
| | 3' | NH$_2$CTCAGCACT-Pi 5' | |
| CD18-Bsl I-ATG | 5' | GATCTCCTAGAGTCGTGAATG 3' | (SEQ ID NO:23) |
| | 3' | NH$_2$CTCAGCACT-Pi 5' | |
| CD18-Bsl I-ATC | 5' | GATCTCCTAGAGTCGTGAATC 3' | (SEQ ID NO:24) |
| | 3' | NH$_2$CTCAGCACT-Pi 5' | |
| CD18-Bsl I-ATT | 5' | GATCTCCTAGAGTCGTGAATT 3' | (SEQ ID NO:25) |
| | 3' | NH$_2$CTCAGCACT-Pi 5' | |
| CD18-Bsl I-GAA | 5' | GATCTCCTAGAGTCGTGAGAA 3' | (SEQ ID NO:26) |
| | 3' | NH$_2$CTCAGCACT-Pi 5' | |

TABLE 2-continued

| ADAPTER | SEQUENCE | |
|---|---|---|
| CD18-Bsl I-GAG | 5' GATCTCCTAGAGTCGTGAGAG 3' | (SEQ ID NO:27) |
| | 3' NH$_2$CTCAGCACT-Pi 5' | |
| CD18-Bsl I-GAC | 5' GATCTCCTAGAGTCGTGAGAC 3' | (SEQ ID NO:28) |
| | 3' NH$_2$CTCAGCACT-Pi 5' | |
| CD18-Bsl I-GAT | 5' GATCTCCTAGAGTCGTGAGAT 3' | (SEQ ID NO:29) |
| | 3' NH$_2$CTCAGCACT-Pi 5' | |
| CD18-Bsl I-GGA | 5' GATCTCCTAGAGTCGTGAGGA 3' | (SEQ ID NO:30) |
| | 3' NH$_2$CTCAGCACT-Pi 5' | |
| CD18-Bsl I-GGG | 5' GATCTCCTAGAGTCGTGAGGG 3' | (SEQ ID NO:31) |
| | 3' NH$_2$CTCAGCACT-Pi 5' | |
| CD18-Bsl I-GGC | 5' GATCTCCTAGAGTCGTGAGGC 3' | (SEQ ID NO:32) |
| | 3' NH$_2$CTCAGCACT-Pi 5' | |
| CD18-Bsl I-GGT | 5' GATCTCCTAGAGTCGTGAGGT 3' | (SEQ ID NO:33) |
| | 3' NH$_2$CTCAGCACT-Pi 5' | |
| CD18-Bsl I-GCA | 5' GATCTCCTAGAGTCGTGAGCA 3' | (SEQ ID NO:34) |
| | 3' NH$_2$CTCAGCACT-Pi 5' | |
| CD18-Bsl I-GCG | 5' GATCTCCTAGAGTCGTGAGCG 3' | (SEQ ID NO:35) |
| | 3' NH$_2$CTCAGCACT-Pi 5' | |
| CD18-Bsl I-GCC | 5' GATCTCCTAGAGTCGTGAGCC 3' | (SEQ ID NO:36) |
| | 3' NH$_2$CTCAGCACT-Pi 5' | |
| CD18-Bsl I-GCT | 5' GATCTCCTAGAGTCGTGAGCT 3' | (SEQ ID NO:37) |
| | 3' NH$_2$CTCAGCACT-Pi 5' | |
| CD18-Bsl I-GTA | 5' GATCTCCTAGAGTCGTGAGTA 3' | (SEQ ID NO:38) |
| | 3' NH$_2$CTCAGCACT-Pi 5' | |
| CD18-Bsl I-GTG | 5' GATCTCCTAGAGTCGTGAGTG 3' | (SEQ ID NO:39) |
| | 3' NH$_2$CTCAGCACT-Pi 5' | |
| CD18-Bsl I-GTC | 5' GATCTCCTAGAGTCGTGAGTC 3' | (SEQ ID NO:40) |
| | 3' NH$_2$CTCAGCACT-Pi 5' | |
| CD18-Bsl I-GTT | 5' GATCTCCTAGAGTCGTGAGTT 3' | (SEQ ID NO:41) |
| | 3' NH$_2$CTCAGCACT-Pi 5' | |
| CD18-Bsl I-CAA | 5' GATCTCCTAGAGTCGTGACAA 3' | (SEQ ID NO:42) |
| | 3' NH$_2$CTCAGCACT-Pi 5' | |
| CD18-Bsl I-CAG | 5' GATCTCCTAGAGTCGTGACAG 3' | (SEQ ID NO:43) |
| | 3' NH$_2$CTCAGCACT-Pi 5' | |
| CD18-Bsl I-CAC | 5' GATCTCCTAGAGTCGTGACAC 3' | (SEQ ID NO:44) |
| | 3' NH$_2$CTCAGCACT-Pi 5' | |
| CD18-Bsl I-CAT | 5' GATCTCCTAGAGTCGTGACAT 3' | (SEQ ID NO:45) |
| | 3' NH$_2$CTCAGCACT-Pi 5' | |
| CD18-Bsl I-CGA | 5' GATCTCCTAGAGTCGTGACGA 3' | (SEQ ID NO:46) |
| | 3' NH$_2$CTCAGCACT-Pi 5' | |
| CD18-Bsl I-CGG | 5' GATCTCCTAGAGTCGTGACGG 3' | (SEQ ID NO:47) |
| | 3' NH$_2$CTCAGCACT-Pi 5' | |
| CD18-Bsl I-CGC | 5' GATCTCCTAGAGTCGTGACGC 3' | (SEQ ID NO:48) |
| | 3' NH$_2$CTCAGCACT-Pi 5' | |
| CD18-Bsl I-CGT | 5' GATCTCCTAGAGTCGTGACGT 3' | (SEQ ID NO:49) |
| | 3' NH$_2$CTCAGCACT-Pi 5' | |
| CD18-Bsl I-CCA | 5' GATCTCCTAGAGTCGTGACCA 3' | (SEQ ID NO:50) |
| | 3' NH$_2$CTCAGCACT-Pi 5' | |
| CD18-Bsl I-CCG | 5' GATCTCCTAGAGTCGTGACCG 3' | (SEQ ID NO:51) |
| | 3' NH$_2$CTCAGCACT-Pi 5' | |
| CD18-Bsl I-CCC | 5' GATCTCCTAGAGTCGTGACCC 3' | (SEQ ID NO:52) |
| | 3' NH$_2$CTCAGCACT-Pi 5' | |
| CD18-Bsl I-CCT | 5' GATCTCCTAGAGTCGTGACCT 3' | (SEQ ID NO:53) |
| | 3' NH$_2$CTCAGCACT-Pi 5' | |
| CD18-Bsl I-CTA | 5' GATCTCCTAGAGTCGTGACTA 3' | (SEQ ID NO:54) |
| | 3' NH$_2$CTCAGCACT-Pi 5' | |
| CD18-Bsl I-CTG | 5' GATCTCCTAGAGTCGTGACTG 3' | (SEQ ID NO:55) |
| | 3' NH$_2$CTCAGCACT-Pi 5' | |
| CD18-Bsl I-CTC | 5' GATCTCCTAGAGTCGTGACTC 3' | (SEQ ID NO:56) |
| | 3' NH$_2$CTCAGCACT-Pi 5' | |
| CD18-Bsl I-CTT | 5' GATCTCCTAGAGTCGTGACTT 3' | (SEQ ID NO:57) |
| | 3' NH$_2$CTCAGCACT-Pi 5' | |
| CD18-Bsl I-TAA | 5' GATCTCCTAGAGTCGTGATAA 3' | (SEQ ID NO:58) |
| | 3' NH$_2$CTCAGCACT-Pi 5' | |
| CD18-Bsl I-TAG | 5' GATCTCCTAGAGTCGTGATAG 3' | (SEQ ID NO:59) |
| | 3' NH$_2$CTCAGCACT-Pi 5' | |
| CD18-Bsl I-TAC | 5' GATCTCCTAGAGTCGTGATAC 3' | (SEQ ID NO:60) |
| | 3' NH$_2$CTCAGCACT-Pi 5' | |
| CD18-Bsl I-TAT | 5' GATCTCCTAGAGTCGTGATAT 3' | (SEQ ID NO:61) |
| | 3' NH$_2$CTCAGCACT-Pi 5' | |
| CD18-Bsl I-TGA | 5' GATCTCCTAGAGTCGTGATGA 3' | (SEQ ID NO:62) |
| | 3' NH$_2$CTCAGCACT-Pi 5' | |
| CD18-Bsl I-TGG | 5' GATCTCCTAGAGTCGTGATGG 3' | (SEQ ID NO:63) |
| | 3' NH$_2$CTCAGCACT-Pi 5' | |
| CD18-Bsl I-TGC | 5' GATCTCCTAGAGTCGTGATGC 3' | (SEQ ID NO:64) |
| | 3' NH$_2$CTCAGCACT-Pi 5' | |
| CD18-Bsl I-TGT | 5' GATCTCCTAGAGTCGTGATGT 3' | (SEQ ID NO:65) |
| | 3' NH$_2$CTCAGCACT-Pi 5' | |
| CD18-Bsl I-TCA | 5' GATCTCCTAGAGTCGTGATCA 3' | (SEQ ID NO:66) |
| | 3' NH$_2$CTCAGCACT-Pi 5' | |
| CD18-Bsl I-TCG | 5' GATCTCCTAGAGTCGTGATCG 3' | (SEQ ID NO:67) |
| | 3' NH$_2$CTCAGCACT-Pi 5' | |
| CD18-Bsl I-TCC | 5' GATCTCCTAGAGTCGTGATCC 3' | (SEQ ID NO:68) |
| | 3' NH$_2$CTCAGCACT-Pi 5' | |
| CD18-Bsl I-TCT | 5' GATCTCCTAGAGTCGTGATCT 3' | (SEQ ID NO:69) |
| | 3' NH$_2$CTCAGCACT-Pi 5' | |
| CD18-Bsl I-TTA | 5' GATCTCCTAGAGTCGTGATTA 3' | (SEQ ID NO:70) |
| | 3' NH$_2$CTCAGCACT-Pi 5' | |
| CD18-Bsl I-TTG | 5' GATCTCCTAGAGTCGTGATTG 3' | (SEQ ID NO:71) |
| | 3' NH$_2$CTCAGCACT-Pi 5' | |
| CD18-Bsl I-TTC | 5' GATCTCCTAGAGTCGTGATTC 3' | (SEQ ID NO:72) |
| | 3' NH$_2$CTCAGCACT-Pi 5' | |
| CD18-Bsl I-TTT | 5' GATCTCCTAGAGTCGTGATTT 3' | (SEQ ID NO:73) |
| | 3' NH$_2$CTCAGCACT-Pi 5' | |

1.8. Amplification of Adapter-Ligated Fragments

Adapter ligated non-redundant fingerprints (fragments) produced in section 1.7 were transferred to the corresponding wells in 96-well PCR plates on ice. To each column of a plate was added 2.4 μl of the appropriate CD18-Bsl I-NNN primer (10 μM) as shown in Table 4. The CD18-Bsl I-NNN primers comprised the upper strands of the CD18-Bsl I adapters listed in Table 2. Following addition of the CD18-Bsl I-NNN primers the plates were centrifuged briefly at 4°

C., 3000 rpm to bring the contents to the bottom of the well, mixed by gentle vortexing, and placed on ice. Next, 17.6 µl of PCR mix was added to each well, the plates briefly centrifuged at 4° C., 3000 rpm to bring the contents to the bottom of the well and the contents mixed by gentle vortexing. PCR was made by combining 330 µl of 10×PCR buffer (Invitrogen, Carlsbad, Calif.), 99 µl MgCl₂ (50 mM), 66 µl dNTP (10 mM each), 198 µl DMSO, 264 µl 5'-NED-AB18-upper primer, 55 µl Taq DNA polymerase (5 U/µl), and 924 µl nuclease-free water. The 5'-NED-AB18-upper primer had the sequence:

5' NED-gctgctagtgtccgatgt 3' (SEQ ID NO: 74)

where NED is the dye N-(1-napthyl)ethylenediamine (Applied Biosystems, Foster City, Calif.)

After mixing, plates were placed in a thermal cycler with a heated lid and fragments amplified using the following program:

| 1 cycle   | 94° C. | 1 minute    |
|-----------|--------|-------------|
| 30 cycles | 94° C. | 30 seconds  |
|           | 60° C. | 30 seconds  |
|           | 72° C. | 1.5 minutes |
| 1 cycle   | 72° C. | 10 minutes  |
| 1 cycle   | 4° C.  | hold        |

Following amplification, PCR products were run immediately on a sequencing gel or stored at −20° C. in the dark until used.

1.9. Recovery and Direct Sequencing of Non-Redundant Fragments

Separation of the amplified non-redundant fingerprints was carried out using a Genomyx 5.6% denaturing acrylamide gel. To cast a gel, 90 ml of HR-1000 5.6% denaturing gel mix (Genomyx, Foster City, Calif.) was warmed to room temperature and thoroughly mixed with 720 µl of 10% ammonium persulfate. To this was added 72 µl of TEMED and the solution mixed. The gel was then cast immediately using 0.4 mm spacers and the gel allowed to polymerize for at least one hour.

The upper and lower tank buffers for the gel were 0.5× TBE and 1×TBE, respectively. PCR products (3.5 µl) were mixed with 3.2 µl of loading dye (1 gram blue dextran [Sigma #D-5751], 20 µl of 0.5M EDTA, pH 8.0, deionized formamide to 50 ml and 0.5 ml saturated bromphenol blue). The samples were denatured by heating to 95° C. for 5 minutes and then quickly chilled on ice. Six µl of denatured sample was loaded on the gel and electrophoresis carried out at 55° C., 100 W for 2.5 hours. Size standards were included in each gel. Following electrophoresis, the gel plate was scanned using a Genomyx SC Fluorescent Imaging Scanner and the gel image analyzed using Photoshop software. An image of the gel was printed and the bands to be recovered marked.

To recover the bands, the gel was dried and the marked bands excised using the gel image print as a reference. There were, on average, about 35 bands per lane so about 26,880 unique fragments were obtained for each library (35×96 lanes/plate×8 plates). Gel resolution is up to 100 bands, so theoretically, 76,800 unique fragments could be obtained. The gel containing the bands was soaked in low TE buffer (1.0 mM Tris-HCl, pH 7.5, and 0.1 mM EDTA) in PCR tubes and incubated at 37° C. for 2.5 hours and 65° C. for 15 minutes, followed by storage at −20° C.

Bands were amplified by PCR for direct sequencing. Each PCR reaction contained 10 µl of gel recovered DNA, 2 µl of 10×PCR buffer, 0.6 µl MgCl₂ (50 mM), 0.4 µl dNTP (10 mM each), 1 µl M13R-AB18 upper primer (10 µM) (5'-ggaaacagctatgaccatggctgctagtgtccgatgt-3', SEQ ID NO: 75), 1 µl CD18-upper primer (10 µM) (5'-gatctcctagagtcgtga-3', SEQ ID NO: 76), 0.25 µl Taq DNA polymerase (5 U/µl) and 4.75 µl of nuclease-free water for a total volume of 20 µl. The amplification program was as follows:

| 1 cycle   | 94° C. | 3 minutes   |
|-----------|--------|-------------|
| 30 cycles | 94° C. | 30 seconds  |
|           | 56° C. | 30 seconds  |
|           | 72° C. | 1.5 minutes |
| 1 cycle   | 72° C. | 10 minutes  |
| 1 cycle   | 4° C.  | hold        |

Direct sequencing was done performed on 4 µl of Exo-SAP treated PCR products using M13R as a primer. Treatment with a combination of exonuclease I (Exo) and Shrimp Alkaline Phosphatase (SAP) removes excess primers and unincorporated nucleotides (Mamome et al., *Comments*, 21:57–78, 1995). Each sequencing reaction contained 2 µl of Big Dye terminator premix (Applied Biosystems, Foster City, Calif.), 1 µl 5×buffer (Applied Biosystems), 0.5 µl M13R primer (10 µM), 4 µl purified PCR product, and 2.5 µl HPLC grade water for a total volume of 10 µl. PCR was carried out in 96-well PCR plates using the following program.

| 25 cycles | 95° C. | 10 seconds |
|-----------|--------|------------|
|           | 50° C. | 5 seconds  |
|           | 60° C. | 2 minutes  |

Sequencing products were purified as described above. The purified products were denatured at 95° C. for 2 minutes and quickly chilled on ice. The samples were run (injection time 50 sec) in an ABI Prism 3700 DNA analyzer at 50° C., 5250 V for approximately 10,000 seconds.

Example 2

Construction of Non-Redundant Library Using a Single Digestion 2.1. RNA Isolation and cDNA Synthesis RNA isolation and biotinylated cDNA synthesis were as described in sections 1.1, 1.2 and 1.3 of Example 1.

2.2. Restriction Enzyme Digestion

The restriction enzyme used was BsaJ I which has the following degenerate recognition sequence:

5'-C'CNNGG-3'
3'-GGNNC,C-5'

Reactions were set up on ice and contained 3.4 µl of 10×NEBuffer 2 (New England Biolabs), 3.4 µl of 10×BSA (1 mg/ml), 1.6 µl BsaJ I (2.5 U/µl), 4 µl cDNA (~10 ng/µl), and 21.6 µl nuclease-free water, for a total volume of 34 µl. Reactions were carried out at 37° C. for 1.5 hours followed by 60° C. for another 1.5 hours. The digested samples were ligated with adapters immediately or stored at −20° C.

2.3. Selective Adapter Ligation

The adapters used are listed in Table 3. Adapter ligation reactions were performed in 96 well PCR plates. Each well contained 2 µl of digested cDNA (~2.5 ng), 2 µl of one of the 16 BsaJ I adapters (0.05 µM), 2 µl (1.5 U) of DNA ligase in ligase buffer (New England Biolabs, Beverly, Mass.) and 2 µl of nuclease-free water for a total volume of 8 µl. The plates were placed in a thermal cycler with a heated lid and incubated at 16° C. for 2 hours and then heated to 72° C. for 15 minutes. Following ligation, the biotinylated 3' end fragments were enriched by capture on streptavidin-coated beads as described in section 1.5 of Example 1.

TABLE 3

| ADAPTER | | SEQUENCE | |
|---|---|---|---|
| CD18-BsaJ I-tt | 5' | GATCTCCTAGAGTCGTGA 3' | (SEQ ID NO: 77) |
| | 3' | GATCTCAGCACTGTTC 5' | (SEQ ID NO: 78) |
| CD18-BsaJ I-tc | 5' | GATCTCCTAGAGTCGTGA 3' | (SEQ ID NO: 77) |
| | 3' | GATCTCAGCACTGTCC 5' | (SEQ ID NO: 79) |
| CD18-BsaJ I-tg | 5' | GATCTCCTAGAGTCGTGA 3' | (SEQ ID NO: 77) |
| | 3' | GATCTCAGCACTGTGC 5' | (SEQ ID NO: 80) |
| CD18-BsaJ I-ta | 5' | GATCTCCTAGAGTCGTGA 3' | (SEQ ID NO: 77) |
| | 3' | GATCTCAGCACTGTAC 5' | (SEQ ID NO: 81) |
| CD18-BsaJ I-ct | 5' | GATCTCCTAGAGTCGTGA 3' | (SEQ ID NO: 77) |
| | 3' | GATCTCAGCACTGCTC 5' | (SEQ ID NO: 82) |
| CD18-BsaJ I-cc | 5' | GATCTCCTAGAGTCGTGA 3' | (SEQ ID NO: 77) |
| | 3' | GATCTCAGCACTGCCC 5' | (SEQ ID NO: 83) |
| CD18-BsaJ I-cg | 5' | GATCTCCTAGAGTCGTGA 3' | (SEQ ID NO: 77) |
| | 3' | GATCTCAGCACTGCGC 5' | (SEQ ID NO: 84) |
| CD18-BsaJ I-ca | 5' | GATCTCCTAGAGTCGTGA 3' | (SEQ ID NO: 77) |
| | 3' | GATCTCAGCACTGCAC 5' | (SEQ ID NO: 85) |
| CD18-BsaJ I-gt | 5' | GATCTCCTAGAGTCGTGA 3' | (SEQ ID NO: 77) |
| | 3' | GATCTCAGCACTGGTC 5' | (SEQ ID NO: 86) |
| CD18-BsaJ I-gc | 5' | GATCTCCTAGAGTCGTGA 3' | (SEQ ID NO: 77) |
| | 3' | GATCTCAGCACTGGCC 5' | (SEQ ID NO: 87) |
| CD18-BsaJ I-gg | 5' | GATCTCCTAGAGTCGTGA 3' | (SEQ ID NO: 77) |
| | 3' | GATCTCAGCACTGGGC 5' | (SEQ ID NO: 88) |
| CD18-BsaJ I-ga | 5' | GATCTCCTAGAGTCGTGA 3' | (SEQ ID NO: 77) |
| | 3' | GATCTCAGCACTGGAC 5' | (SEQ ID NO: 89) |
| CD18-BsaJ I-at | 5' | GATCTCCTAGAGTCGTGA 3' | (SEQ ID NO: 77) |
| | 3' | GATCTCAGCACTGATC 5' | (SEQ ID NO: 90) |
| CD18-BsaJ I-ac | 5' | GATCTCCTAGAGTCGTGA 3' | (SEQ ID NO: 77) |
| | 3' | GATCTCAGCACTGACC 5' | (SEQ ID NO: 91) |
| CD18-BsaJ I-ag | 5' | GATCTCCTAGAGTCGTGA 3' | (SEQ ID NO: 77) |
| | 3' | GATCTCAGCACTGAGC 5' | (SEQ ID NO: 92) |
| CD18BsaJ I-aa | 5' | GATCTCCTAGAGTCGTGA 3' | (SEQ ID NO: 77) |
| | 3' | GATCTCAGCACTGAAC 5' | (SEQ ID NO: 93) |

2.4. Amplification of Adapter-Ligated Fragments

PCR amplification was carried out as described in section 1.8 of Example 1 with the following changes. The primers used were 5' NED-gctgctagtgtccgatgt 3' (SEQ ID NO: 74) used in Example 1 and one of the 16 possible CD18-BsaJ I-NN primers comprising the lower stands of the double stranded adapters listed in Table 3. The amplification program used was as follows:

| 1 cycle | 72° C. | 5 minutes |
|---|---|---|
| 25 cycles | 94° C. | 30 seconds, ramp to 56° C. at 1° C./second |
| | 56° C. | 30 seconds, ramp to 72° C. at 1° C./second |
| | 72° C. | 1.5 minutes |
| 1 cycle | 72° C. | 10 minutes |
| 1 cycle | 4° C. | hold |

The extent of fractionation of the 3'-end restriction fragments can be further increased by using a 5'-end primer that incorporates an additional degenerate base at the 3'-end of the primer. For example, following is a list of 64 kinds of CD18-BsaJ I-NNGGN (N=degenerate base) primers that can be used for selective PCR, wherein the first two degenerate bases are derived from the BsaJI recognition site and the third (3' terminal) degenerate base is an extra base added to achieve further fractionation. Thus, there are 64 distinct primers ($4^3$=64) that can be used for PCR amplification. It is important to note that separate PCR reactions are carried out with each of these primers. The bases at degenerate positions are identified by bold type.

5' GATCTCCTAGAGTCGTGACAAGGA 3' (SEQ ID NO:94)

5' GATCTCCTAGAGTCGTGACAAGGT 3' (SEQ ID NO:95)

5' GATCTCCTAGAGTCGTGACAAGGG 3' (SEQ ID NO:96)

5' GATCTCCTAGAGTCGTGACAAGGC 3' (SEQ ID NO:97)

5' GATCTCCTAGAGTCGTGACAGGGA 3' (SEQ ID NO:98)

5' GATCTCCTAGAGTCGTGACAGGGT 3' (SEQ ID NO:99)

5' GATCTCCTAGAGTCGTGACAGGGG 3' (SEQ ID NO:100)

5' GATCTCCTAGAGTCGTGACAGGGC 3' (SEQ ID NO:101)

5' GATCTCCTAGAGTCGTGACACGGA 3' (SEQ ID NO:102)

5' GATCTCCTAGAGTCGTGACACGGT 3' (SEQ ID NO:103)

5' GATCTCCTAGAGTCGTGACACGGG 3' (SEQ ID NO:104)

5' GATCTCCTAGAGTCGTGACACGGC 3' (SEQ ID NO:105)

5' GATCTCCTAGAGTCGTGACATGGA 3' (SEQ ID NO:106)

```
5' GATCTCCTAGAGTCGTGACATGGT 3' (SEQ ID NO:107)
5' GATCTCCTAGAGTCGTGACATGGG 3' (SEQ ID NO:108)
5' GATCTCCTAGAGTCGTGACATGGC 3' (SEQ ID NO:109)
5' GATCTCCTAGAGTCGTGACGAGGA 3' (SEQ ID NO:110)
5' GATCTCCTAGAGTCGTGACGAGGT 3' (SEQ ID NO:111)
5' GATCTCCTAGAGTCGTGACGAGGG 3' (SEQ ID NO:112)
5' GATCTCCTAGAGTCGTGACGAGGC 3' (SEQ ID NO:113)
5' GATCTCCTAGAGTCGTGACGGGGA 3' (SEQ ID NO:114)
5' GATCTCCTAGAGTCGTGACGGGGT 3' (SEQ ID NO:115)
5' GATCTCCTAGAGTCGTGACGGGGG 3' (SEQ ID NO:116)
5' GATCTCCTAGAGTCGTGACGGGGC 3' (SEQ ID NO:117)
5' GATCTCCTAGAGTCGTGACGCGGA 3' (SEQ ID NO:118)
5' GATCTCCTAGAGTCGTGACGCGGT 3' (SEQ ID NO:119)
5' GATCTCCTAGAGTCGTGACGCGGG 3' (SEQ ID NO:120)
5' GATCTCCTAGAGTCGTGACGCGGC 3' (SEQ ID NO:121)
5' GATCTCCTAGAGTCGTGACGTGGA 3' (SEQ ID NO:122)
5' GATCTCCTAGAGTCGTGACGTGGT 3' (SEQ ID NO:123)
5' GATCTCCTAGAGTCGTGACGTGGG 3' (SEQ ID NO:124)
5' GATCTCCTAGAGTCGTGACGTGGC 3' (SEQ ID NO:125)
5' GATCTCCTAGAGTCGTGACCAGGA 3' (SEQ ID NO:126)
5' GATCTCCTAGAGTCGTGACCAGGT 3' (SEQ ID NO:127)
5' GATCTCCTAGAGTCGTGACCAGGG 3' (SEQ ID NO:128)
5' GATCTCCTAGAGTCGTGACCAGGC 3' (SEQ ID NO:129)
5' GATCTCCTAGAGTCGTGACCGGGA 3' (SEQ ID NO:130)
5' GATCTCCTAGAGTCGTGACCGGGT 3' (SEQ ID NO:131)
5' GATCTCCTAGAGTCGTGACCGGGG 3' (SEQ ID NO:132)
5' GATCTCCTAGAGTCGTGACCGGGC 3' (SEQ ID NO:133)
5' GATCTCCTAGAGTCGTGACCCGGA 3' (SEQ ID NO:134)
5' GATCTCCTAGAGTCGTGACCCGGT 3' (SEQ ID NO:135)
5' GATCTCCTAGAGTCGTGACCCGGG 3' (SEQ ID NO:136)
5' GATCTCCTAGAGTCGTGACCCGGC 3' (SEQ ID NO:137)
5' GATCTCCTAGAGTCGTGACCTGGA 3' (SEQ ID NO:138)
5' GATCTCCTAGAGTCGTGACCTGGT 3' (SEQ ID NO:139)
5' GATCTCCTAGAGTCGTGACCTGGG 3' (SEQ ID NO:140)
5' GATCTCCTAGAGTCGTGACCTGGC 3' (SEQ ID NO:141)
5' GATCTCCTAGAGTCGTGACTAGGA 3' (SEQ ID NO:142)
5' GATCTCCTAGAGTCGTGACTAGGT 3' (SEQ ID NO:143)
5' GATCTCCTAGAGTCGTGACTAGGG 3' (SEQ ID NO:144)
5' GATCTCCTAGAGTCGTGACTAGGC 3' (SEQ ID NO:145)
5' GATCTCCTAGAGTCGTGACTGGGA 3' (SEQ ID NO:146)
5' GATCTCCTAGAGTCGTGACTGGGT 3' (SEQ ID NO:147)
5' GATCTCCTAGAGTCGTGACTGGGG 3' (SEQ ID NO:148)
5' GATCTCCTAGAGTCGTGACTGGGC 3' (SEQ ID NO:149)
5' GATCTCCTAGAGTCGTGACTCGGA 3' (SEQ ID NO:150)
5' GATCTCCTAGAGTCGTGACTCGGT 3' (SEQ ID NO:151)
5' GATCTCCTAGAGTCGTGACTCGGG 3' (SEQ ID NO:152)
5' GATCTCCTAGAGTCGTGACTCGGC 3' (SEQ ID NO:153)
5' GATCTCCTAGAGTCGTGACTTGGA 3' (SEQ ID NO:154)
5' GATCTCCTAGAGTCGTGACTTGGT 3' (SEQ ID NO:155)
5' GATCTCCTAGAGTCGTGACTTGGG 3' (SEQ ID NO:156)
5' GATCTCCTAGAGTCGTGACTTGGC 3' (SEQ ID NO:157)
```

2.6. Recovery and Direct Sequencing of Non-Redundant Fragments

Recovery and direct sequencing of fragments was similar to that described in section 1.9 of Example 1 with the following changes. Amplification of fragments recovered from gels was accomplished using M13R-CD18-BsaJ I primer (ggaaacagctatgaccatcgatctcctagagtcgtga, SEQ ID NO: 158) and the M13F-Seq1 primer (tgtaaaacgacggccagtgctgctagtgtccgatgt, SEQ ID NO: 159). The amplification program was the same as in section 2.4. DNA sequencing PCR was the same except that both M13F (tgtaaaacgacggccagt SEQ ID NO: 160) or M13R (ggaaacagctatgaccatc SEQ ID NO: 161) primers were used.

TABLE 4

| | 6RE ---> Bs/I | | | | | | Bs/I ---> 6RE | | | | | |
|---|---|---|---|---|---|---|---|---|---|---|---|---|
| | 1 | 2 | 3 | 4 | 5 | 6 | 7 | 8 | 9 | 10 | 11 | 12 |
| | Apa L I | Bam HI | Eco R I | Hind III | Nco I | Xho I | Apa L I | Bam HI | Eco R I | Hind III | Nco I | Xho I |
| Plate 1 | | | | | | | | | | | | |
| A | AAA | AAA | AAA | AAA | AAA | AAA | AAA | AAA | AAA | AAA | AAA | AAA |
| B | AAG | AAG | AAG | AAG | AAG | AAG | AAG | AAG | AAG | AAG | AAG | AAG |
| C | AAC | AAC | AAC | AAC | AAC | AAC | AAC | AAC | AAC | AAC | AAC | AAC |
| D | AAT | AAT | AAT | AAT | AAT | AAT | AAT | AAT | AAT | AAT | AAT | AAT |
| E | AGA | AGA | AGA | AGA | AGA | AGA | AGA | AGA | AGA | AGA | AGA | AGA |
| F | AGG | AGG | AGG | AGG | AGG | AGG | AGG | AGG | AGG | AGG | AGG | AGG |

TABLE 4-continued

|   | 6RE ---> Bs/I | | | | | | Bs/I --> 6RE | | | | | |
|---|---|---|---|---|---|---|---|---|---|---|---|---|
|   | 1 Apa L I | 2 Bam HI | 3 Eco R I | 4 Hind III | 5 Nco I | 6 Xho I | 7 Apa L I | 8 Bam HI | 9 Eco R I | 10 Hind III | 11 Nco I | 12 Xho I |
| G | AGC | AGC | AGC | AGC | AGC | AGC | AGC | AGC | AGC | AGC | AGC | AGC |
| H | AGT | AGT | AGT | AGT | AGT | AGT | AGT | AGT | AGT | AGT | AGT | AGT |

Plate 2

| | | | | | | | | | | | | |
|---|---|---|---|---|---|---|---|---|---|---|---|---|
| A | ACA | ACA | ACA | ACA | ACA | ACA | ACA | ACA | ACA | ACA | ACA | ACA |
| B | ACG | ACG | ACG | ACG | ACG | ACA | ACG | ACG | ACG | ACG | ACG | ACA |
| C | ACC | ACC | ACC | ACC | ACC | ACC | ACC | ACC | ACC | ACC | ACC | ACC |
| D | ACT | ACT | ACT | ACT | ACT | ACT | ACT | ACT | ACT | ACT | ACT | ACT |
| E | ATA | ATA | ATA | ATA | ATA | ATA | ATA | ATA | ATA | ATA | ATA | ATA |
| F | ATG | ATG | ATG | ATG | ATG | ATG | ATG | ATG | ATG | ATG | ATG | ATG |
| G | ATC | ATC | ATC | ATC | ATC | ATC | ATC | ATC | ATC | ATC | ATC | ATC |
| H | ATT | ATT | ATT | ATT | ATT | ATT | ATT | ATT | ATT | ATT | ATT | ATT |

Plate 3

| | | | | | | | | | | | | |
|---|---|---|---|---|---|---|---|---|---|---|---|---|
| A | GAA | GAA | GAA | GAA | GAA | GAA | GAA | GAA | GAA | GAA | GAA | GAA |
| B | GAG | GAG | GAG | GAG | GAG | GAG | GAG | GAG | GAG | GAG | GAG | GAG |
| C | GAC | GAC | GAC | GAC | GAC | GAC | GAC | GAC | GAC | GAC | GAC | GAC |
| D | GAT | GAT | GAT | GAT | GAT | GAT | GAT | GAT | GAT | GAT | GAT | GAT |
| E | GGA | GGA | GGA | GGA | GGA | GGA | GGA | GGA | GGA | GGA | GGA | GGA |
| F | GGG | GGG | GGG | GGG | GGG | GGG | GGG | GGG | GGG | GGG | GGG | GGG |
| G | GGC | GGC | GGC | GGC | GGC | GGC | GGC | GGC | GGC | GGC | GGC | GGC |
| H | GGT | GGT | GGT | GGT | GGT | GGT | GGT | GGT | GGT | GGT | GGT | GGT |

Plate 4

| | | | | | | | | | | | | |
|---|---|---|---|---|---|---|---|---|---|---|---|---|
| A | GCA | GCA | GCA | GCA | GCA | GCA | GCA | GCA | GCA | GCA | GCA | GCA |
| B | GCG | GCG | GCG | GCG | GCG | GCG | GCG | GCG | GCG | GCG | GCG | GCG |
| C | GCC | GCC | GCC | GCC | GCC | GCC | GCC | GCC | GCC | GCC | GCC | GCC |
| D | GCT | GCT | GCT | GCT | GCT | GCT | GCT | GCT | GCT | GCT | GCT | GCT |
| E | GTA | GTA | GTA | GTA | GTA | GTA | GTA | GTA | GTA | GTA | GTA | GTA |
| F | GTG | GTG | GTG | GTG | GTG | GTG | GTG | GTG | GTG | GTG | GTG | GTG |
| G | GTC | GTC | GTC | GTC | GTC | GTC | GTC | GTC | GTC | GTC | GTC | GTC |
| H | GTT | GTT | GTT | GTT | GTT | GTT | GTT | GTT | GTT | GTT | GTT | GTT |

Plate 5

| | | | | | | | | | | | | |
|---|---|---|---|---|---|---|---|---|---|---|---|---|
| A | CAA | CAA | CAA | CAA | CAA | CAA | CAA | CAA | CAA | CAA | CAA | CAA |
| B | CAG | CAG | CAG | CAG | CAG | CAG | CAG | CAG | CAG | CAG | CAG | CAG |
| C | CAC | CAC | CAC | CAC | CAC | CAC | CAC | CAC | CAC | CAC | CAC | CAC |
| D | CAT | CAT | CAT | CAT | CAT | CAT | CAT | CAT | CAT | CAT | CAT | CAT |
| E | CGA | CGA | CGA | CGA | CGA | CGA | CGA | CGA | CGA | CGA | CGA | CGA |
| F | CGG | CGG | CGG | CGG | CGG | CGG | CGG | CGG | CGG | CGG | CGG | CGG |
| G | CGC | CGC | CGC | CGC | CGC | CGC | CGC | CGC | CGC | CGC | CGC | CGC |
| H | CGT | CGT | CGT | CGT | CGT | CGT | CGT | CGT | CGT | CGT | CGT | CGT |

Plate 6

| | | | | | | | | | | | | |
|---|---|---|---|---|---|---|---|---|---|---|---|---|
| A | CCA | CCA | CCA | CCA | CCA | CCA | CCA | CCA | CCA | CCA | CCA | CCA |
| B | CCG | CCG | CCG | CCG | CCG | CCG | CCG | CCG | CCG | CCG | CCG | CCG |
| C | CCC | CCC | CCC | CCC | CCC | CCC | CCC | CCC | CCC | CCC | CCC | CCC |
| D | CCT | CCT | CCT | CCT | CCT | CCT | CCT | CCT | CCT | CCT | CCT | CCT |
| E | CTA | CTA | CTA | CTA | CTA | CTA | CTA | CTA | CTA | CTA | CTA | CTA |
| F | CTG | CTG | CTG | CTG | CTG | CTG | CTG | CTG | CTG | CTG | CTG | CTG |
| G | CTC | CTC | CTC | CTC | CTC | CTC | CTC | CTC | CTC | CTC | CTC | CTC |
| H | CTT | CTT | CTT | CTT | CTT | CTT | CTT | CTT | CTT | CTT | CTT | CTT |

Plate 7

| | | | | | | | | | | | | |
|---|---|---|---|---|---|---|---|---|---|---|---|---|
| A | TAA | TAA | TAA | TAA | TAA | TAA | TAA | TAA | TAA | TAA | TAA | TAA |
| B | TAG | TAG | TAG | TAG | TAG | TAG | TAG | TAG | TAG | TAG | TAG | TAG |
| C | TAC | TAC | TAC | TAC | TAC | TAC | TAC | TAC | TAC | TAC | TAC | TAC |
| D | TAT | TAT | TAT | TAT | TAT | TAT | TAT | TAT | TAT | TAT | TAT | TAT |
| E | TGA | TGA | TGA | TGA | TGA | TGA | TGA | TGA | TGA | TGA | TGA | TGA |
| F | TGG | TGG | TGG | TGG | TGG | TGG | TGG | TGG | TGG | TGG | TGG | TGG |
| G | TGC | TGC | TGC | TGC | TGC | TGC | TGC | TGC | TGC | TGC | TGC | TGC |
| H | TGT | TGT | TGT | TGT | TGT | TGT | TGT | TGT | TGT | TGT | TGT | TGT |

Plate 8

| | | | | | | | | | | | | |
|---|---|---|---|---|---|---|---|---|---|---|---|---|
| A | TCA | TCA | TCA | TCA | TCA | TCA | TCA | TCA | TCA | TCA | TCA | TCA |
| B | TCG | TCG | TCG | TCG | TCG | TCG | TCG | TCG | TCG | TCG | TCG | TCG |
| C | TCC | TCC | TCC | TCC | TCC | TCC | TCC | TCC | TCC | TCC | TCC | TCC |
| D | TCT | TCT | TCT | TCT | TCT | TCT | TCT | TCT | TCT | TCT | TCT | TCT |
| E | TTA | TTA | TTA | TTA | TTA | TTA | TTA | TTA | TTA | TTA | TTA | TTA |
| F | TTG | TTG | TTG | TTG | TTG | TTG | TTG | TTG | TTG | TTG | TTG | TTG |
| G | TTC | TTC | TTC | TTC | TTC | TTC | TTC | TTC | TTC | TTC | TTC | TTC |
| H | TTT | TTT | TTT | TTT | TTT | TTT | TTT | TTT | TTT | TTT | TTT | TTT |

CONCLUSION

In light of the detailed description and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method for constructing a nucleic acid library comprising:
   a) obtaining a population of end-labeled double-stranded cDNA molecules;
   b) dividing said population into a first portion and a second portion;
   c) digesting said first portion with at least one sequence-specific endonuclease wherein said first portion is divided into one pool per endonuclease;
   d) digesting said second portion with at least one (Y) endonuclease having a degenerate recognition sequence and fractionating the digested cDNA into $YX^z$ pools where Y is the number of degenerate endonucleases, X is the the extent of degeneracy and z is the number of bases;
   e) isolating nucleic acid fragments from said endonuclease digestions of said first and second portions using said end-labels;
   f) digesting the fragments of said first portion with said at least one endonuclease of d) sequence and fractionating the digested cDNA into $YX^z$ pools where Y is the number of degenerate endonucleases, X is the the extent of degeneracy and z is the number of bases;
   g) digesting the fragments of said second portion with said at least one endonuclease of c) wherein the second portion pools are divided into one pool per endonuclease;

h) removing labeled nucleic acid fragments from said first and second portions while retaining unlabeled fragments;

i) adding a population of adapters to each of the pools, said population containing adapters specific for the endonucleases used, wherein each adapter comprises a first region specific to a particular endonuclease used and a second region containing a primer binding site;

j) hybridizing and ligating said adapters to said unlabeled fragments;

k) amplifying the fragments using the adapters; and l) separating the amplified fragments by size.

2. The method of claim 1, wherein said at least one sequence-specific endonuclease comprises at least 4 different sequence specific endonucleases.

3. The method of claim 1, wherein said at least one sequence-specific endonuclease comprises at least 6 different sequence specific endonucleases.

4. The method of claim 1, wherein said at least one sequence-specific endonuclease is selected from the group consisting of at least one endonuclease having a 4 base recognition sequence, at least one endonuclease having a 5 base recognition sequence and at least one endonuclease having a 6 base recognition sequence.

5. The method of claim 3, wherein said at least one sequence-specific endonuclease is selected from the group consisting of Apa LI, Bam HI, Eco RI, Hind III, Nco I, and Xho I.

6. The method of claim 1, wherein said at least one endonuclease having a degenerate recognition sequence produces fragments comprising unpaired overhangs containing $N^m$ unique sequences where N is the extent of degeneracy and is an integer between 2 and 4, and m is the number of bases in said unpaired overhang and is an integer between 2 and 6.

7. The method of claim 6, wherein $N^m$ equals at least 64.

8. The method of claim 7 wherein said endonuclease is Bsl I.

9. The method of claim 1, further comprising sequencing the separated fragments of I).

10. The method of claim 1, further comprising quantifying the separated fragments of I).

11. The method of claim 1, wherein said primer binding region of said adapters does not have significant homology to sequences known to be in said population of nucleic acid molecules.

12. The method of claim 11, wherein said primer binding regions of said adapters comprise no more than 10 different sequences.

13. The method of claim 12, wherein said primer binding region comprise no more than two different sequences.

14. The method of claim 1, wherein said end-labeled nucleic acid molecules are obtained by a method comprising, isolating polyA mRNA from a cell; hybridizing a 5' end labeled an oligo dT primer to said polyA mRNA; synthesizing a first cDNA strand by extension of said primer; and synthesizing a second cDNA strand by nick translation to produce double stranded cDNA.

15. The method of claim 14, wherein said oligo dT primer has a sequence comprising L-$(T)_n$VN, where L is a label at the 5' end of said primer and n is an integer between 4 and 50.

16. The method of claim 14, wherein said at least one sequence-specific endonuclease comprises at least 4 different endonucleases.

17. The method of claim 14, wherein said at least one sequence-specific endonuclease is selected from the group consisting of at least one endonuclease having a 4 base recognition sequence, at least one endonuclease having a 5 base recognition sequence and at least one endonuclease having a six base recognition sequence.

18. The method of claim 14, wherein said at least one sequence-specific endonuclease comprises at least 6 different endonucleases.

19. The method of claim 18, wherein said at least one sequence-specific endonuclease is selected from the group consisting of Apa LI, Bam HI, Eco RI, Hind III, Nco I, and Xho I.

20. The method of claim 14, wherein said at least one endonuclease having a degenerate recognition sequence produces fragments comprising unpaired overhangs containing $N^m$ unique sequences where N is the extent of degeneracy and is an integer between 2 and 4, and m is the number of bases in said unpaired overhang and is an integer between 2 and 6.

21. The method of claim 20, wherein $N^m$ equals at least 64.

22. The method of claim 21 wherein said endonuclease is Bsl I.

23. The method of claim 14, wherein said label is biotin.

24. The method of claim 14, wherein isolating and removing of end-labeled nucleic acid molecules is by particles that bind said end-labeled nucleic acid molecules.

25. The method of claim 24, wherein said end-label is biotin and said particles comprise avidin or strepavidin.

26. The method of claim 14, further comprising sequencing the separated fragments of I).

27. The method of claim 14, further comprising quantifying the separated fragments of I).

28. A method for constructing a nucleic acid library comprising:

a) obtaining a population of 3' end-labeled double-stranded cDNA molecules by a method comprising, isolating polyA mRNA from a cell; hybridizing a 5' end labeled primer containing an oligo dT tail to said polyA mRNA; synthesizing a first cDNA strand by extension of said primer; and synthesizing a second cDNA strand by nick translation to produce a double stranded cDNA;

b) dividing said labeled population into a first portion and a second portion;

c) digesting said first portion with at least one sequence-specific endonuclease selected from the group consisting of at least one endonuclease having a 4 base recognition sequence, at least one endonuclease having a 5 base recognition sequence and at least one endonuclease having a six base recognition sequence wherein said first portion is divided into one pool per endonuclease;

d) digesting said second portion with at least one endonuclease having a degenerate recognition sequence wherein said endonuclease produces fragments comprising unpaired overhangs containing $N^m$ unique sequences where N is an integer between 2 and 4, m is an integer between 2 and 6, and $N^m$ equals at least 64 and fractionating the digested cDNA into $YX^z$ pools where Y is the number of degenerate endonucleases, X is the extent of degeneracy and z is the number of bases;

e) isolating nucleic acid fragments from said endonuclease digestions of said first and second portions using said end-labels;

f) digesting the fragments of said first portion with said at least one endonuclease of d) and fractionating the digested cDNA into $YX^z$ pools where Y is the number of degenerate endonucleases, X is the extent of degeneracy and z is the number of bases;

g) digesting the fragments of said second portion with said at least one endonuclease of c) wherein said first portion is divided into one pool per endonuclease;

h) removing labeled nucleic acid fragments from said first and second portions while retaining unlabeled fragments;

i) adding a population of adapters to each of the pools, said population containing adapters specific for at least some of the endonucleases used, wherein each adapter comprises a first region specific to a particular endonuclease used and a second region containing a primer binding site, said primer binding sites comprising no more than 10 different sequences, said sequences lacking significant homology to sequences known to be in said population of nucleic acid molecules;

j) hybridizing and ligating said adapters to said unlabeled fragments;

k) amplifying said unlabeled fragments using the adapters; and l) separating the amplified fragments on the basis of size.

29. The method of claim 28, wherein said at least one sequence-specific endonuclease comprises at least 4 endonucleases.

30. The method of claim 28, wherein said at least one sequence-specific endonuclease comprises at least 6 endonucleases.

31. The method of claim 30, wherein said at least one sequence-specific endonuclease is selected from the group consisting of Apa LI, Bam HI, Eco RI, Hind III, Nco I, and Xho I.

32. The method of claim 28, wherein said at least one endonuclease having a degenerate recognition sequence is Bsl I.

33. The method of claim 28, wherein said at least one sequence-specific endonuclease is selected from the group consisting of Apa LI, Bam HI, Eco RI, Hind III, Nco I, and Xho I, and said at least one endonuclease having a degenerate recognition sequence is Bsl I.

34. The method of claim 28, wherein said adapters comprise a common primer binding site.

35. The method of claim 28, further comprising sequencing the separated fragments of 1).

36. The method of claim 28, further comprising quantifying the separated fragments of I).

37. The method of claim 28, wherein said label is biotin.

38. The method of claim 28, wherein isolating and removing of end-labeled nucleic acid molecules is by particles that bind said end-labeled nucleic acid molecules.

39. The method of claim 38, wherein said end-label is biotin and said particles comprise avidin or strepavidin.

40. A method for constructing a nucleic acid library comprising:

a) obtaining a population of double stranded cDNA wherein cDNA molecules contained in said population contain a detectable label on their 3' end;

b) digesting said double-stranded cDNA with at least one restriction endonuclease having a degenerate recognition sequence comprising at least one degenerate base, wherein said digestion creates a single-stranded portion or overhang containing a region having the formula $N^m$, where N is the extent of degeneracy and m is the number of degenerate bases in said single stranded portion or overhang to produce digestion fragments and fractionating the digested cDNA into $YX^z$ pools where Y is the number of degenerate endonucleases, X is the extent of degeneracy and z is the number of bases;

c) adding a population of adapters to each of the pools, said adapters specific for the at least one endonuclease used;

d) hybridizing and ligating said adapters to the 5' end of said digestions fragments;

e) separating said 3' end digestion fragments using said detectable label;

f) amplifying said 3' end digestion fragments;

g) separating said amplified digestion fragments on the basis of size.

41. The method of claim 40, wherein said adapters contain first region specific to a particular endonuclease and a second primer binding region common to all adapters.

42. The method of claim 40, wherein $N^m$ equals at least 16.

43. The method of claim 42, wherein said at least one endonuclease is BsaJ I.

* * * * *

SEQUENCE LISTING

```
<160> NUMBER OF SEQ ID NOS: 161

<210> SEQ ID NO 1
<211> LENGTH: 18
<212> TYPE: DNA
<213> ORGANISM: Artificial Sequence
<220> FEATURE:
<223> OTHER INFORMATION: Adapter

<400> SEQUENCE: 1
gctgctagtg tccgatgt                                                 18

<210> SEQ ID NO 2
<211> LENGTH: 18
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: n = any nucleotide
      Adapter

<400> SEQUENCE: 2
nnnnacatcg gacactag                                                 18

<210> SEQ ID NO 3
<211> LENGTH: 18
<212> TYPE: DNA
<213> ORGANISM: Artificial Sequence
<220> FEATURE:
<223> OTHER INFORMATION: Adapter

<400> SEQUENCE: 3
gctgctagtg tccgatgt                                                 18

<210> SEQ ID NO 4
<211> LENGTH: 18
<212> TYPE: DNA
<213> ORGANISM: Artificial Sequence
<220> FEATURE:
<223> OTHER INFORMATION: Adapter

<400> SEQUENCE: 4
tgcaacatcg gacactag                                                 18

<210> SEQ ID NO 5
<211> LENGTH: 18
<212> TYPE: DNA
<213> ORGANISM: Artificial Sequence
<220> FEATURE:
```

```
<223> OTHER INFORMATION: Adapter

<400> SEQUENCE: 5
gatcacatcg gacactag                                                    18

<210> SEQ ID NO 6
<211> LENGTH: 18
<212> TYPE: DNA
<213> ORGANISM: Artificial Sequence
<220> FEATURE:
<223> OTHER INFORMATION: Adapter

<400> SEQUENCE: 6
aattacatcg gacactag                                                    18

<210> SEQ ID NO 7
<211> LENGTH: 18
<212> TYPE: DNA
<213> ORGANISM: Artificial Sequence
<220> FEATURE:
<223> OTHER INFORMATION: Adapter

<400> SEQUENCE: 7
agctacatcg gacactag                                                    18

<210> SEQ ID NO 8
<211> LENGTH: 18
<212> TYPE: DNA
<213> ORGANISM: Artificial Sequence
<220> FEATURE:
<223> OTHER INFORMATION: Adapter

<400> SEQUENCE: 8
catgacatcg gacactag                                                    18

<210> SEQ ID NO 9
<211> LENGTH: 18
<212> TYPE: DNA
<213> ORGANISM: Artificial Sequence
<220> FEATURE:
<223> OTHER INFORMATION: Adapter

<400> SEQUENCE: 9
agctacatcg gacactag                                                    18

<210> SEQ ID NO 10
<211> LENGTH: 21
<212> TYPE: DNA
<213> ORGANISM: Artificial Sequence
<220> FEATURE:
<223> OTHER INFORMATION: Adapter

<400> SEQUENCE: 10
gatctcctag agtcgtgaaa a                                                21

<210> SEQ ID NO 11
<211> LENGTH: 21
<212> TYPE: DNA
<213> ORGANISM: Artificial Sequence
<220> FEATURE:
<223> OTHER INFORMATION: Adapter

<400> SEQUENCE: 11
gatctcctag agtcgtgaaa g                                                21
```

```
<210> SEQ ID NO 12
<211> LENGTH: 21
<212> TYPE: DNA
<213> ORGANISM: Artificial Sequence
<220> FEATURE:
<223> OTHER INFORMATION: Adapter

<400> SEQUENCE: 12
gatctcctag agtcgtgaaa c                                              21

<210> SEQ ID NO 13
<211> LENGTH: 21
<212> TYPE: DNA
<213> ORGANISM: Artificial Sequence
<220> FEATURE:
<223> OTHER INFORMATION: Adapter

<400> SEQUENCE: 13
gatctcctag agtcgtgaaa t                                              21

<210> SEQ ID NO 14
<211> LENGTH: 21
<212> TYPE: DNA
<213> ORGANISM: Artificial Sequence
<220> FEATURE:
<223> OTHER INFORMATION: Adapter

<400> SEQUENCE: 14
gatctcctag agtcgtgaag a                                              21

<210> SEQ ID NO 15
<211> LENGTH: 21
<212> TYPE: DNA
<213> ORGANISM: Artificial Sequence
<220> FEATURE:
<223> OTHER INFORMATION: Adapter

<400> SEQUENCE: 15
gatctcctag agtcgtgaag g                                              21

<210> SEQ ID NO 16
<211> LENGTH: 21
<212> TYPE: DNA
<213> ORGANISM: Artificial Sequence
<220> FEATURE:
<223> OTHER INFORMATION: Adapter

<400> SEQUENCE: 16
gatctcctag agtcgtgaag c                                              21

<210> SEQ ID NO 17
<211> LENGTH: 21
<212> TYPE: DNA
<213> ORGANISM: Artificial Sequence
<220> FEATURE:
<223> OTHER INFORMATION: Adapter

<400> SEQUENCE: 17
gatctcctag agtcgtgaag t                                              21

<210> SEQ ID NO 18
<211> LENGTH: 21
<212> TYPE: DNA
<213> ORGANISM: Artificial Sequence
<220> FEATURE:
<223> OTHER INFORMATION: Adapter
```

```
<400> SEQUENCE: 18
gatctcctag agtcgtgaac a                                              21

<210> SEQ ID NO 19
<211> LENGTH: 21
<212> TYPE: DNA
<213> ORGANISM: Artificial Sequence
<220> FEATURE:
<223> OTHER INFORMATION: Adapter

<400> SEQUENCE: 19
gatctcctag agtcgtgaac g                                              21

<210> SEQ ID NO 20
<211> LENGTH: 21
<212> TYPE: DNA
<213> ORGANISM: Artificial Sequence
<220> FEATURE:
<223> OTHER INFORMATION: Adapter

<400> SEQUENCE: 20
gatctcctag agtcgtgaac c                                              21

<210> SEQ ID NO 21
<211> LENGTH: 21
<212> TYPE: DNA
<213> ORGANISM: Artificial Sequence
<220> FEATURE:
<223> OTHER INFORMATION: Adapter

<400> SEQUENCE: 21
gatctcctag agtcgtgaac t                                              21

<210> SEQ ID NO 22
<211> LENGTH: 21
<212> TYPE: DNA
<213> ORGANISM: Artificial Sequence
<220> FEATURE:
<223> OTHER INFORMATION: Adapter

<400> SEQUENCE: 22
gatctcctag agtcgtgaat a                                              21

<210> SEQ ID NO 23
<211> LENGTH: 21
<212> TYPE: DNA
<213> ORGANISM: Artificial Sequence
<220> FEATURE:
<223> OTHER INFORMATION: Adapter

<400> SEQUENCE: 23
gatctcctag agtcgtgaat g                                              21

<210> SEQ ID NO 24
<211> LENGTH: 21
<212> TYPE: DNA
<213> ORGANISM: Artificial Sequence
<220> FEATURE:
<223> OTHER INFORMATION: Adapter

<400> SEQUENCE: 24
gatctcctag agtcgtgaat c                                              21

<210> SEQ ID NO 25
<211> LENGTH: 21
```

```
<212> TYPE: DNA
<213> ORGANISM: Artificial Sequence
<220> FEATURE:
<223> OTHER INFORMATION: Adapter

<400> SEQUENCE: 25
gatctcctag agtcgtgaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Adapter

<400> SEQUENCE: 26
gatctcctag agtcgtgaga a                                              21

<210> SEQ ID NO 27
<211> LENGTH: 21
<212> TYPE: DNA
<213> ORGANISM: Artificial Sequence
<220> FEATURE:
<223> OTHER INFORMATION: Adapter

<400> SEQUENCE: 27
gatctcctag agtcgtgaga g                                              21

<210> SEQ ID NO 28
<211> LENGTH: 21
<212> TYPE: DNA
<213> ORGANISM: Artificial Sequence
<220> FEATURE:
<223> OTHER INFORMATION: Adapter

<400> SEQUENCE: 28
gatctcctag agtcgtgaga c                                              21

<210> SEQ ID NO 29
<211> LENGTH: 21
<212> TYPE: DNA
<213> ORGANISM: Artificial Sequence
<220> FEATURE:
<223> OTHER INFORMATION: Adapter

<400> SEQUENCE: 29
gatctcctag agtcgtgaga t                                              21

<210> SEQ ID NO 30
<211> LENGTH: 21
<212> TYPE: DNA
<213> ORGANISM: Artificial Sequence
<220> FEATURE:
<223> OTHER INFORMATION: Adapter

<400> SEQUENCE: 30
gatctcctag agtcgtgagg a                                              21

<210> SEQ ID NO 31
<211> LENGTH: 21
<212> TYPE: DNA
<213> ORGANISM: Artificial Sequence
<220> FEATURE:
<223> OTHER INFORMATION: Adapter

<400> SEQUENCE: 31
```

```
gatctcctag agtcgtgagg g                                              21
```

<210> SEQ ID NO 32
<211> LENGTH: 21
<212> TYPE: DNA
<213> ORGANISM: Artificial Sequence
<220> FEATURE:
<223> OTHER INFORMATION: Adapter

<400> SEQUENCE: 32

```
gatctcctag agtcgtgagg c                                              21
```

<210> SEQ ID NO 33
<211> LENGTH: 21
<212> TYPE: DNA
<213> ORGANISM: Artificial Sequence
<220> FEATURE:
<223> OTHER INFORMATION: Adapter

<400> SEQUENCE: 33

```
gatctcctag agtcgtgagg t                                              21
```

<210> SEQ ID NO 34
<211> LENGTH: 21
<212> TYPE: DNA
<213> ORGANISM: Artificial Sequence
<220> FEATURE:
<223> OTHER INFORMATION: Adapter

<400> SEQUENCE: 34

```
gatctcctag agtcgtgagc a                                              21
```

<210> SEQ ID NO 35
<211> LENGTH: 21
<212> TYPE: DNA
<213> ORGANISM: Artificial Sequence
<220> FEATURE:
<223> OTHER INFORMATION: Adapter

<400> SEQUENCE: 35

```
gatctcctag agtcgtgagc g                                              21
```

<210> SEQ ID NO 36
<211> LENGTH: 21
<212> TYPE: DNA
<213> ORGANISM: Artificial Sequence
<220> FEATURE:
<223> OTHER INFORMATION: Adapter

<400> SEQUENCE: 36

```
gatctcctag agtcgtgagc c                                              21
```

<210> SEQ ID NO 37
<211> LENGTH: 21
<212> TYPE: DNA
<213> ORGANISM: Artificial Sequence
<220> FEATURE:
<223> OTHER INFORMATION: Adapter

<400> SEQUENCE: 37

```
gatctcctag agtcgtgagc t                                              21
```

<210> SEQ ID NO 38
<211> LENGTH: 21
<212> TYPE: DNA
<213> ORGANISM: Artificial Sequence

```
<220> FEATURE:
<223> OTHER INFORMATION: Adapter

<400> SEQUENCE: 38
gatctcctag agtcgtgagt a                                              21

<210> SEQ ID NO 39
<211> LENGTH: 21
<212> TYPE: DNA
<213> ORGANISM: Artificial Sequence
<220> FEATURE:
<223> OTHER INFORMATION: Adapter

<400> SEQUENCE: 39
gatctcctag agtcgtgagt g                                              21

<210> SEQ ID NO 40
<211> LENGTH: 21
<212> TYPE: DNA
<213> ORGANISM: Artificial Sequence
<220> FEATURE:
<223> OTHER INFORMATION: Adapter

<400> SEQUENCE: 40
gatctcctag agtcgtgagt c                                              21

<210> SEQ ID NO 41
<211> LENGTH: 21
<212> TYPE: DNA
<213> ORGANISM: Artificial Sequence
<220> FEATURE:
<223> OTHER INFORMATION: Adapter

<400> SEQUENCE: 41
gatctcctag agtcgtgagt t                                              21

<210> SEQ ID NO 42
<211> LENGTH: 21
<212> TYPE: DNA
<213> ORGANISM: Artificial Sequence
<220> FEATURE:
<223> OTHER INFORMATION: Adapter

<400> SEQUENCE: 42
gatctcctag agtcgtgaca a                                              21

<210> SEQ ID NO 43
<211> LENGTH: 21
<212> TYPE: DNA
<213> ORGANISM: Artificial Sequence
<220> FEATURE:
<223> OTHER INFORMATION: Adapter

<400> SEQUENCE: 43
gatctcctag agtcgtgaca g                                              21

<210> SEQ ID NO 44
<211> LENGTH: 21
<212> TYPE: DNA
<213> ORGANISM: Artificial Sequence
<220> FEATURE:
<223> OTHER INFORMATION: Adapter

<400> SEQUENCE: 44
gatctcctag agtcgtgaca c                                              21
```

-continued

<210> SEQ ID NO 45
<211> LENGTH: 21
<212> TYPE: DNA
<213> ORGANISM: Artificial Sequence
<220> FEATURE:
<223> OTHER INFORMATION: Adapter

<400> SEQUENCE: 45
gatctcctag agtcgtgaca t                                              21

<210> SEQ ID NO 46
<211> LENGTH: 21
<212> TYPE: DNA
<213> ORGANISM: Artificial Sequence
<220> FEATURE:
<223> OTHER INFORMATION: Adapter

<400> SEQUENCE: 46
gatctcctag agtcgtgacg a                                              21

<210> SEQ ID NO 47
<211> LENGTH: 21
<212> TYPE: DNA
<213> ORGANISM: Artificial Sequence
<220> FEATURE:
<223> OTHER INFORMATION: Adapter

<400> SEQUENCE: 47
gatctcctag agtcgtgacg g                                              21

<210> SEQ ID NO 48
<211> LENGTH: 21
<212> TYPE: DNA
<213> ORGANISM: Artificial Sequence
<220> FEATURE:
<223> OTHER INFORMATION: Adapter

<400> SEQUENCE: 48
gatctcctag agtcgtgacg c                                              21

<210> SEQ ID NO 49
<211> LENGTH: 21
<212> TYPE: DNA
<213> ORGANISM: Artificial Sequence
<220> FEATURE:
<223> OTHER INFORMATION: Adapter

<400> SEQUENCE: 49
gatctcctag agtcgtgacg t                                              21

<210> SEQ ID NO 50
<211> LENGTH: 21
<212> TYPE: DNA
<213> ORGANISM: Artificial Sequence
<220> FEATURE:
<223> OTHER INFORMATION: Adapter

<400> SEQUENCE: 50
gatctcctag agtcgtgacc a                                              21

<210> SEQ ID NO 51
<211> LENGTH: 21
<212> TYPE: DNA
<213> ORGANISM: Artificial Sequence
<220> FEATURE:
<223> OTHER INFORMATION: Adapter

<400> SEQUENCE: 51
gatctcctag agtcgtgacc g                                         21

<210> SEQ ID NO 52
<211> LENGTH: 21
<212> TYPE: DNA
<213> ORGANISM: Artificial Sequence
<220> FEATURE:
<223> OTHER INFORMATION: Adapter

<400> SEQUENCE: 52
gatctcctag agtcgtgacc c                                         21

<210> SEQ ID NO 53
<211> LENGTH: 21
<212> TYPE: DNA
<213> ORGANISM: Artificial Sequence
<220> FEATURE:
<223> OTHER INFORMATION: Adapter

<400> SEQUENCE: 53
gatctcctag agtcgtgacc t                                         21

<210> SEQ ID NO 54
<211> LENGTH: 21
<212> TYPE: DNA
<213> ORGANISM: Artificial Sequence
<220> FEATURE:
<223> OTHER INFORMATION: Adapter

<400> SEQUENCE: 54
gatctcctag agtcgtgact a                                         21

<210> SEQ ID NO 55
<211> LENGTH: 21
<212> TYPE: DNA
<213> ORGANISM: Artificial Sequence
<220> FEATURE:
<223> OTHER INFORMATION: Adapter

<400> SEQUENCE: 55
gatctcctag agtcgtgact g                                         21

<210> SEQ ID NO 56
<211> LENGTH: 21
<212> TYPE: DNA
<213> ORGANISM: Artificial Sequence
<220> FEATURE:
<223> OTHER INFORMATION: Adapter

<400> SEQUENCE: 56
gatctcctag agtcgtgact c                                         21

<210> SEQ ID NO 57
<211> LENGTH: 21
<212> TYPE: DNA
<213> ORGANISM: Artificial Sequence
<220> FEATURE:
<223> OTHER INFORMATION: Adapter

<400> SEQUENCE: 57
gatctcctag agtcgtgact t                                         21

<210> SEQ ID NO 58

<211> LENGTH: 21
<212> TYPE: DNA
<213> ORGANISM: Artificial Sequence
<220> FEATURE:
<223> OTHER INFORMATION: Adapter

<400> SEQUENCE: 58
gatctcctag agtcgtgata a                                               21

<210> SEQ ID NO 59
<211> LENGTH: 21
<212> TYPE: DNA
<213> ORGANISM: Artificial Sequence
<220> FEATURE:
<223> OTHER INFORMATION: Adapter

<400> SEQUENCE: 59
gatctcctag agtcgtgata g                                               21

<210> SEQ ID NO 60
<211> LENGTH: 21
<212> TYPE: DNA
<213> ORGANISM: Artificial Sequence
<220> FEATURE:
<223> OTHER INFORMATION: Adapter

<400> SEQUENCE: 60
gatctcctag agtcgtgata c                                               21

<210> SEQ ID NO 61
<211> LENGTH: 21
<212> TYPE: DNA
<213> ORGANISM: Artificial Sequence
<220> FEATURE:
<223> OTHER INFORMATION: Adapter

<400> SEQUENCE: 61
gatctcctag agtcgtgata t                                               21

<210> SEQ ID NO 62
<211> LENGTH: 21
<212> TYPE: DNA
<213> ORGANISM: Artificial Sequence
<220> FEATURE:
<223> OTHER INFORMATION: Adapter

<400> SEQUENCE: 62
gatctcctag agtcgtgatg a                                               21

<210> SEQ ID NO 63
<211> LENGTH: 21
<212> TYPE: DNA
<213> ORGANISM: Artificial Sequence
<220> FEATURE:
<223> OTHER INFORMATION: Adapter

<400> SEQUENCE: 63
gatctcctag agtcgtgatg g                                               21

<210> SEQ ID NO 64
<211> LENGTH: 21
<212> TYPE: DNA
<213> ORGANISM: Artificial Sequence
<220> FEATURE:
<223> OTHER INFORMATION: Adapter

<400> SEQUENCE: 64
gatctcctag agtcgtgatg c                                              21

<210> SEQ ID NO 65
<211> LENGTH: 21
<212> TYPE: DNA
<213> ORGANISM: Artificial Sequence
<220> FEATURE:
<223> OTHER INFORMATION: Adapter

<400> SEQUENCE: 65
gatctcctag agtcgtgatg t                                              21

<210> SEQ ID NO 66
<211> LENGTH: 21
<212> TYPE: DNA
<213> ORGANISM: Artificial Sequence
<220> FEATURE:
<223> OTHER INFORMATION: Adapter

<400> SEQUENCE: 66
gatctcctag agtcgtgatc a                                              21

<210> SEQ ID NO 67
<211> LENGTH: 21
<212> TYPE: DNA
<213> ORGANISM: Artificial Sequence
<220> FEATURE:
<223> OTHER INFORMATION: Adapter

<400> SEQUENCE: 67
gatctcctag agtcgtgatc g                                              21

<210> SEQ ID NO 68
<211> LENGTH: 21
<212> TYPE: DNA
<213> ORGANISM: Artificial Sequence
<220> FEATURE:
<223> OTHER INFORMATION: Adapter

<400> SEQUENCE: 68
gatctcctag agtcgtgatc c                                              21

<210> SEQ ID NO 69
<211> LENGTH: 21
<212> TYPE: DNA
<213> ORGANISM: Artificial Sequence
<220> FEATURE:
<223> OTHER INFORMATION: Adapter

<400> SEQUENCE: 69
gatctcctag agtcgtgatc t                                              21

<210> SEQ ID NO 70
<211> LENGTH: 21
<212> TYPE: DNA
<213> ORGANISM: Artificial Sequence
<220> FEATURE:
<223> OTHER INFORMATION: Adapter

<400> SEQUENCE: 70
gatctcctag agtcgtgatt a                                              21

<210> SEQ ID NO 71
<211> LENGTH: 21
<212> TYPE: DNA

<213> ORGANISM: Artificial Sequence
<220> FEATURE:
<223> OTHER INFORMATION: Adapter

<400> SEQUENCE: 71
gatctcctag agtcgtgatt g                                         21

<210> SEQ ID NO 72
<211> LENGTH: 21
<212> TYPE: DNA
<213> ORGANISM: Artificial Sequence
<220> FEATURE:
<223> OTHER INFORMATION: Adapter

<400> SEQUENCE: 72
gatctcctag agtcgtgatt c                                         21

<210> SEQ ID NO 73
<211> LENGTH: 21
<212> TYPE: DNA
<213> ORGANISM: Artificial Sequence
<220> FEATURE:
<223> OTHER INFORMATION: Adapter

<400> SEQUENCE: 73
gatctcctag agtcgtgatt t                                         21

<210> SEQ ID NO 74
<211> LENGTH: 18
<212> TYPE: DNA
<213> ORGANISM: Artificial Sequence
<220> FEATURE:
<223> OTHER INFORMATION: Primer

<400> SEQUENCE: 74
gctgctagtg tccgatgt                                             18

<210> SEQ ID NO 75
<211> LENGTH: 37
<212> TYPE: DNA
<213> ORGANISM: Artificial Sequence
<220> FEATURE:
<223> OTHER INFORMATION: Primer

<400> SEQUENCE: 75
ggaaacagct atgaccatgg ctgctagtgt ccgatgt                        37

<210> SEQ ID NO 76
<211> LENGTH: 18
<212> TYPE: DNA
<213> ORGANISM: Artificial Sequence
<220> FEATURE:
<223> OTHER INFORMATION: Primer

<400> SEQUENCE: 76
gatctcctag agtcgtga                                             18

<210> SEQ ID NO 77
<211> LENGTH: 18
<212> TYPE: DNA
<213> ORGANISM: Artificial Sequence
<220> FEATURE:
<223> OTHER INFORMATION: Adapter

<400> SEQUENCE: 77
gatctcctag agtcgtga                                             18

<210> SEQ ID NO 78
<211> LENGTH: 16
<212> TYPE: DNA
<213> ORGANISM: Artificial Sequence
<220> FEATURE:
<223> OTHER INFORMATION: Adapter

<400> SEQUENCE: 78
cttgtcacga ctctag                                                    16

<210> SEQ ID NO 79
<211> LENGTH: 16
<212> TYPE: DNA
<213> ORGANISM: Artificial Sequence
<220> FEATURE:
<223> OTHER INFORMATION: Adapter

<400> SEQUENCE: 79
cctgtcacga ctctag                                                    16

<210> SEQ ID NO 80
<211> LENGTH: 16
<212> TYPE: DNA
<213> ORGANISM: Artificial Sequence
<220> FEATURE:
<223> OTHER INFORMATION: Adapter

<400> SEQUENCE: 80
cgtgtcacga ctctag                                                    16

<210> SEQ ID NO 81
<211> LENGTH: 16
<212> TYPE: DNA
<213> ORGANISM: Artificial Sequence
<220> FEATURE:
<223> OTHER INFORMATION: Adapter

<400> SEQUENCE: 81
catgtcacga ctctag                                                    16

<210> SEQ ID NO 82
<211> LENGTH: 16
<212> TYPE: DNA
<213> ORGANISM: Artificial Sequence
<220> FEATURE:
<223> OTHER INFORMATION: Adapter

<400> SEQUENCE: 82
ctcgtcacga ctctag                                                    16

<210> SEQ ID NO 83
<211> LENGTH: 16
<212> TYPE: DNA
<213> ORGANISM: Artificial Sequence
<220> FEATURE:
<223> OTHER INFORMATION: Adapter

<400> SEQUENCE: 83
cccgtcacga ctctag                                                    16

<210> SEQ ID NO 84
<211> LENGTH: 16
<212> TYPE: DNA
<213> ORGANISM: Artificial Sequence
<220> FEATURE:

-continued

<223> OTHER INFORMATION: Adapter

<400> SEQUENCE: 84
cgcgtcacga ctctag                                                  16

<210> SEQ ID NO 85
<211> LENGTH: 16
<212> TYPE: DNA
<213> ORGANISM: Artificial Sequence
<220> FEATURE:
<223> OTHER INFORMATION: Adapter

<400> SEQUENCE: 85
cacgtcacga ctctag                                                  16

<210> SEQ ID NO 86
<211> LENGTH: 16
<212> TYPE: DNA
<213> ORGANISM: Artificial Sequence
<220> FEATURE:
<223> OTHER INFORMATION: Adapter

<400> SEQUENCE: 86
ctggtcacga ctctag                                                  16

<210> SEQ ID NO 87
<211> LENGTH: 16
<212> TYPE: DNA
<213> ORGANISM: Artificial Sequence
<220> FEATURE:
<223> OTHER INFORMATION: Adapter

<400> SEQUENCE: 87
ccggtcacga ctctag                                                  16

<210> SEQ ID NO 88
<211> LENGTH: 16
<212> TYPE: DNA
<213> ORGANISM: Artificial Sequence
<220> FEATURE:
<223> OTHER INFORMATION: Adapter

<400> SEQUENCE: 88
cgggtcacga ctctag                                                  16

<210> SEQ ID NO 89
<211> LENGTH: 16
<212> TYPE: DNA
<213> ORGANISM: Artificial Sequence
<220> FEATURE:
<223> OTHER INFORMATION: Adapter

<400> SEQUENCE: 89
caggtcacga ctctag                                                  16

<210> SEQ ID NO 90
<211> LENGTH: 16
<212> TYPE: DNA
<213> ORGANISM: Artificial Sequence
<220> FEATURE:
<223> OTHER INFORMATION: Adapter

<400> SEQUENCE: 90
ctagtcacga ctctag                                                  16

-continued

```
<210> SEQ ID NO 91
<211> LENGTH: 16
<212> TYPE: DNA
<213> ORGANISM: Artificial Sequence
<220> FEATURE:
<223> OTHER INFORMATION: Adapter

<400> SEQUENCE: 91
ccagtcacga ctctag                                                         16

<210> SEQ ID NO 92
<211> LENGTH: 16
<212> TYPE: DNA
<213> ORGANISM: Artificial Sequence
<220> FEATURE:
<223> OTHER INFORMATION: Adapter

<400> SEQUENCE: 92
cgagtcacga ctctag                                                         16

<210> SEQ ID NO 93
<211> LENGTH: 16
<212> TYPE: DNA
<213> ORGANISM: Artificial Sequence
<220> FEATURE:
<223> OTHER INFORMATION: Adapter

<400> SEQUENCE: 93
caagtcacga ctctag                                                         16

<210> SEQ ID NO 94
<211> LENGTH: 24
<212> TYPE: DNA
<213> ORGANISM: Artificial Sequence
<220> FEATURE:
<223> OTHER INFORMATION: Primer

<400> SEQUENCE: 94
gatctcctag agtcgtgaca agga                                                24

<210> SEQ ID NO 95
<211> LENGTH: 24
<212> TYPE: DNA
<213> ORGANISM: Artificial Sequence
<220> FEATURE:
<223> OTHER INFORMATION: Primer

<400> SEQUENCE: 95
gatctcctag agtcgtgaca aggt                                                24

<210> SEQ ID NO 96
<211> LENGTH: 24
<212> TYPE: DNA
<213> ORGANISM: Artificial Sequence
<220> FEATURE:
<223> OTHER INFORMATION: Primer

<400> SEQUENCE: 96
gatctcctag agtcgtgaca aggg                                                24

<210> SEQ ID NO 97
<211> LENGTH: 24
<212> TYPE: DNA
<213> ORGANISM: Artificial Sequence
<220> FEATURE:
<223> OTHER INFORMATION: Primer
```

```
<400> SEQUENCE: 97
gatctcctag agtcgtgaca aggc                                        24

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
gatctcctag agtcgtgaca ggga                                        24

<210> SEQ ID NO 99
<211> LENGTH: 24
<212> TYPE: DNA
<213> ORGANISM: Artificial Sequence
<220> FEATURE:
<223> OTHER INFORMATION: Primer

<400> SEQUENCE: 99
gatctcctag agtcgtgaca gggt                                        24

<210> SEQ ID NO 100
<211> LENGTH: 24
<212> TYPE: DNA
<213> ORGANISM: Artificial Sequence
<220> FEATURE:
<223> OTHER INFORMATION: Primer

<400> SEQUENCE: 100
gatctcctag agtcgtgaca gggg                                        24

<210> SEQ ID NO 101
<211> LENGTH: 24
<212> TYPE: DNA
<213> ORGANISM: Artificial Sequence
<220> FEATURE:
<223> OTHER INFORMATION: Primer

<400> SEQUENCE: 101
gatctcctag agtcgtgaca gggc                                        24

<210> SEQ ID NO 102
<211> LENGTH: 24
<212> TYPE: DNA
<213> ORGANISM: Artificial Sequence
<220> FEATURE:
<223> OTHER INFORMATION: Primer

<400> SEQUENCE: 102
gatctcctag agtcgtgaca cgga                                        24

<210> SEQ ID NO 103
<211> LENGTH: 24
<212> TYPE: DNA
<213> ORGANISM: Artificial Sequence
<220> FEATURE:
<223> OTHER INFORMATION: Primer

<400> SEQUENCE: 103
gatctcctag agtcgtgaca cggt                                        24

<210> SEQ ID NO 104
<211> LENGTH: 24
```

```
<212> TYPE: DNA
<213> ORGANISM: Artificial Sequence
<220> FEATURE:
<223> OTHER INFORMATION: Primer

<400> SEQUENCE: 104
gatctcctag agtcgtgaca cggg                                          24

<210> SEQ ID NO 105
<211> LENGTH: 24
<212> TYPE: DNA
<213> ORGANISM: Artificial Sequence
<220> FEATURE:
<223> OTHER INFORMATION: Primer

<400> SEQUENCE: 105
gatctcctag agtcgtgaca cggc                                          24

<210> SEQ ID NO 106
<211> LENGTH: 24
<212> TYPE: DNA
<213> ORGANISM: Artificial Sequence
<220> FEATURE:
<223> OTHER INFORMATION: Primer

<400> SEQUENCE: 106
gatctcctag agtcgtgaca tgga                                          24

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
gatctcctag agtcgtgaca tggt                                          24

<210> SEQ ID NO 108
<211> LENGTH: 24
<212> TYPE: DNA
<213> ORGANISM: Artificial Sequence
<220> FEATURE:
<223> OTHER INFORMATION: Primer

<400> SEQUENCE: 108
gatctcctag agtcgtgaca tggg                                          24

<210> SEQ ID NO 109
<211> LENGTH: 24
<212> TYPE: DNA
<213> ORGANISM: Artificial Sequence
<220> FEATURE:
<223> OTHER INFORMATION: Primer

<400> SEQUENCE: 109
gatctcctag agtcgtgaca tggc                                          24

<210> SEQ ID NO 110
<211> LENGTH: 24
<212> TYPE: DNA
<213> ORGANISM: Artificial Sequence
<220> FEATURE:
<223> OTHER INFORMATION: Primer

<400> SEQUENCE: 110
```

-continued gatctcctag agtcgtgacg agga                                    24

<210> SEQ ID NO 111
<211> LENGTH: 24
<212> TYPE: DNA
<213> ORGANISM: Artificial Sequence
<220> FEATURE:
<223> OTHER INFORMATION: Primer

<400> SEQUENCE: 111
gatctcctag agtcgtgacg aggt                                    24

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
gatctcctag agtcgtgacg aggg                                    24

<210> SEQ ID NO 113
<211> LENGTH: 24
<212> TYPE: DNA
<213> ORGANISM: Artificial Sequence
<220> FEATURE:
<223> OTHER INFORMATION: Primer

<400> SEQUENCE: 113
gatctcctag agtcgtgacg aggc                                    24

<210> SEQ ID NO 114
<211> LENGTH: 24
<212> TYPE: DNA
<213> ORGANISM: Artificial Sequence
<220> FEATURE:
<223> OTHER INFORMATION: Primer

<400> SEQUENCE: 114
gatctcctag agtcgtgacg ggga                                    24

<210> SEQ ID NO 115
<211> LENGTH: 24
<212> TYPE: DNA
<213> ORGANISM: Artificial Sequence
<220> FEATURE:
<223> OTHER INFORMATION: Primer

<400> SEQUENCE: 115
gatctcctag agtcgtgacg gggt                                    24

<210> SEQ ID NO 116
<211> LENGTH: 24
<212> TYPE: DNA
<213> ORGANISM: Artificial Sequence
<220> FEATURE:
<223> OTHER INFORMATION: Primer

<400> SEQUENCE: 116
gatctcctag agtcgtgacg gggg                                    24

<210> SEQ ID NO 117
<211> LENGTH: 24
<212> TYPE: DNA
<213> ORGANISM: Artificial Sequence

```
<220> FEATURE:
<223> OTHER INFORMATION: Primer

<400> SEQUENCE: 117
gatctcctag agtcgtgacg gggc                                          24

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118
gatctcctag agtcgtgacg cgga                                          24

<210> SEQ ID NO 119
<211> LENGTH: 24
<212> TYPE: DNA
<213> ORGANISM: Artificial Sequence
<220> FEATURE:
<223> OTHER INFORMATION: Primer

<400> SEQUENCE: 119
gatctcctag agtcgtgacg cggt                                          24

<210> SEQ ID NO 120
<211> LENGTH: 24
<212> TYPE: DNA
<213> ORGANISM: Artificial Sequence
<220> FEATURE:
<223> OTHER INFORMATION: Primer

<400> SEQUENCE: 120
gatctcctag agtcgtgacg cggg                                          24

<210> SEQ ID NO 121
<211> LENGTH: 24
<212> TYPE: DNA
<213> ORGANISM: Artificial Sequence
<220> FEATURE:
<223> OTHER INFORMATION: Primer

<400> SEQUENCE: 121
gatctcctag agtcgtgacg cggc                                          24

<210> SEQ ID NO 122
<211> LENGTH: 24
<212> TYPE: DNA
<213> ORGANISM: Artificial Sequence
<220> FEATURE:
<223> OTHER INFORMATION: Primer

<400> SEQUENCE: 122
gatctcctag agtcgtgacg tgga                                          24

<210> SEQ ID NO 123
<211> LENGTH: 24
<212> TYPE: DNA
<213> ORGANISM: Artificial Sequence
<220> FEATURE:
<223> OTHER INFORMATION: Primer

<400> SEQUENCE: 123
gatctcctag agtcgtgacg tggt                                          24
```

```
<210> SEQ ID NO 124
<211> LENGTH: 24
<212> TYPE: DNA
<213> ORGANISM: Artificial Sequence
<220> FEATURE:
<223> OTHER INFORMATION: Primer

<400> SEQUENCE: 124
gatctcctag agtcgtgacg tggg                                    24

<210> SEQ ID NO 125
<211> LENGTH: 24
<212> TYPE: DNA
<213> ORGANISM: Artificial Sequence
<220> FEATURE:
<223> OTHER INFORMATION: Primer

<400> SEQUENCE: 125
gatctcctag agtcgtgacg tggc                                    24

<210> SEQ ID NO 126
<211> LENGTH: 24
<212> TYPE: DNA
<213> ORGANISM: Artificial Sequence
<220> FEATURE:
<223> OTHER INFORMATION: Primer

<400> SEQUENCE: 126
gatctcctag agtcgtgacc agga                                    24

<210> SEQ ID NO 127
<211> LENGTH: 24
<212> TYPE: DNA
<213> ORGANISM: Artificial Sequence
<220> FEATURE:
<223> OTHER INFORMATION: Primer

<400> SEQUENCE: 127
gatctcctag agtcgtgacc aggt                                    24

<210> SEQ ID NO 128
<211> LENGTH: 24
<212> TYPE: DNA
<213> ORGANISM: Artificial Sequence
<220> FEATURE:
<223> OTHER INFORMATION: Primer

<400> SEQUENCE: 128
gatctcctag agtcgtgacc aggg                                    24

<210> SEQ ID NO 129
<211> LENGTH: 24
<212> TYPE: DNA
<213> ORGANISM: Artificial Sequence
<220> FEATURE:
<223> OTHER INFORMATION: Primer

<400> SEQUENCE: 129
gatctcctag agtcgtgacc aggc                                    24

<210> SEQ ID NO 130
<211> LENGTH: 24
<212> TYPE: DNA
<213> ORGANISM: Artificial Sequence
<220> FEATURE:
<223> OTHER INFORMATION: Primer
```

```
<400> SEQUENCE: 130
gatctcctag agtcgtgacc ggga                                          24

<210> SEQ ID NO 131
<211> LENGTH: 24
<212> TYPE: DNA
<213> ORGANISM: Artificial Sequence
<220> FEATURE:
<223> OTHER INFORMATION: Primer

<400> SEQUENCE: 131
gatctcctag agtcgtgacc gggt                                          24

<210> SEQ ID NO 132
<211> LENGTH: 24
<212> TYPE: DNA
<213> ORGANISM: Artificial Sequence
<220> FEATURE:
<223> OTHER INFORMATION: Primer

<400> SEQUENCE: 132
gatctcctag agtcgtgacc gggg                                          24

<210> SEQ ID NO 133
<211> LENGTH: 24
<212> TYPE: DNA
<213> ORGANISM: Artificial Sequence
<220> FEATURE:
<223> OTHER INFORMATION: Primer

<400> SEQUENCE: 133
gatctcctag agtcgtgacc gggc                                          24

<210> SEQ ID NO 134
<211> LENGTH: 24
<212> TYPE: DNA
<213> ORGANISM: Artificial Sequence
<220> FEATURE:
<223> OTHER INFORMATION: Primer

<400> SEQUENCE: 134
gatctcctag agtcgtgacc cgga                                          24

<210> SEQ ID NO 135
<211> LENGTH: 24
<212> TYPE: DNA
<213> ORGANISM: Artificial Sequence
<220> FEATURE:
<223> OTHER INFORMATION: Primer

<400> SEQUENCE: 135
gatctcctag agtcgtgacc cggt                                          24

<210> SEQ ID NO 136
<211> LENGTH: 24
<212> TYPE: DNA
<213> ORGANISM: Artificial Sequence
<220> FEATURE:
<223> OTHER INFORMATION: Primer

<400> SEQUENCE: 136
gatctcctag agtcgtgacc cggg                                          24

<210> SEQ ID NO 137
```

<211> LENGTH: 24
<212> TYPE: DNA
<213> ORGANISM: Artificial Sequence
<220> FEATURE:
<223> OTHER INFORMATION: Primer

<400> SEQUENCE: 137
gatctcctag agtcgtgacc cggc                                          24

<210> SEQ ID NO 138
<211> LENGTH: 24
<212> TYPE: DNA
<213> ORGANISM: Artificial Sequence
<220> FEATURE:
<223> OTHER INFORMATION: Primer

<400> SEQUENCE: 138
gatctcctag agtcgtgacc tgga                                          24

<210> SEQ ID NO 139
<211> LENGTH: 24
<212> TYPE: DNA
<213> ORGANISM: Artificial Sequence
<220> FEATURE:
<223> OTHER INFORMATION: Primer

<400> SEQUENCE: 139
gatctcctag agtcgtgacc tggt                                          24

<210> SEQ ID NO 140
<211> LENGTH: 24
<212> TYPE: DNA
<213> ORGANISM: Artificial Sequence
<220> FEATURE:
<223> OTHER INFORMATION: Primer

<400> SEQUENCE: 140
gatctcctag agtcgtgacc tggg                                          24

<210> SEQ ID NO 141
<211> LENGTH: 24
<212> TYPE: DNA
<213> ORGANISM: Artificial Sequence
<220> FEATURE:
<223> OTHER INFORMATION: Primer

<400> SEQUENCE: 141
gatctcctag agtcgtgacc tggc                                          24

<210> SEQ ID NO 142
<211> LENGTH: 24
<212> TYPE: DNA
<213> ORGANISM: Artificial Sequence
<220> FEATURE:
<223> OTHER INFORMATION: Primer

<400> SEQUENCE: 142
gatctcctag agtcgtgact agga                                          24

<210> SEQ ID NO 143
<211> LENGTH: 24
<212> TYPE: DNA
<213> ORGANISM: Artificial Sequence
<220> FEATURE:
<223> OTHER INFORMATION: Primer

<400> SEQUENCE: 143
gatctcctag agtcgtgact aggt                                      24

<210> SEQ ID NO 144
<211> LENGTH: 24
<212> TYPE: DNA
<213> ORGANISM: Artificial Sequence
<220> FEATURE:
<223> OTHER INFORMATION: Primer

<400> SEQUENCE: 144
gatctcctag agtcgtgact aggg                                      24

<210> SEQ ID NO 145
<211> LENGTH: 24
<212> TYPE: DNA
<213> ORGANISM: Artificial Sequence
<220> FEATURE:
<223> OTHER INFORMATION: Primer

<400> SEQUENCE: 145
gatctcctag agtcgtgact aggc                                      24

<210> SEQ ID NO 146
<211> LENGTH: 24
<212> TYPE: DNA
<213> ORGANISM: Artificial Sequence
<220> FEATURE:
<223> OTHER INFORMATION: Primer

<400> SEQUENCE: 146
gatctcctag agtcgtgact ggga                                      24

<210> SEQ ID NO 147
<211> LENGTH: 24
<212> TYPE: DNA
<213> ORGANISM: Artificial Sequence
<220> FEATURE:
<223> OTHER INFORMATION: Primer

<400> SEQUENCE: 147
gatctcctag agtcgtgact gggt                                      24

<210> SEQ ID NO 148
<211> LENGTH: 24
<212> TYPE: DNA
<213> ORGANISM: Artificial Sequence
<220> FEATURE:
<223> OTHER INFORMATION: Primer

<400> SEQUENCE: 148
gatctcctag agtcgtgact gggg                                      24

<210> SEQ ID NO 149
<211> LENGTH: 24
<212> TYPE: DNA
<213> ORGANISM: Artificial Sequence
<220> FEATURE:
<223> OTHER INFORMATION: Primer

<400> SEQUENCE: 149
gatctcctag agtcgtgact gggc                                      24

<210> SEQ ID NO 150
<211> LENGTH: 24
<212> TYPE: DNA

<213> ORGANISM: Artificial Sequence
<220> FEATURE:
<223> OTHER INFORMATION: Primer

<400> SEQUENCE: 150
gatctcctag agtcgtgact cgga                                    24

<210> SEQ ID NO 151
<211> LENGTH: 24
<212> TYPE: DNA
<213> ORGANISM: Artificial Sequence
<220> FEATURE:
<223> OTHER INFORMATION: Primer

<400> SEQUENCE: 151
gatctcctag agtcgtgact cggt                                    24

<210> SEQ ID NO 152
<211> LENGTH: 24
<212> TYPE: DNA
<213> ORGANISM: Artificial Sequence
<220> FEATURE:
<223> OTHER INFORMATION: Primer

<400> SEQUENCE: 152
gatctcctag agtcgtgact cggg                                    24

<210> SEQ ID NO 153
<211> LENGTH: 24
<212> TYPE: DNA
<213> ORGANISM: Artificial Sequence
<220> FEATURE:
<223> OTHER INFORMATION: Primer

<400> SEQUENCE: 153
gatctcctag agtcgtgact cggc                                    24

<210> SEQ ID NO 154
<211> LENGTH: 24
<212> TYPE: DNA
<213> ORGANISM: Artificial Sequence
<220> FEATURE:
<223> OTHER INFORMATION: Primer

<400> SEQUENCE: 154
gatctcctag agtcgtgact tgga                                    24

<210> SEQ ID NO 155
<211> LENGTH: 24
<212> TYPE: DNA
<213> ORGANISM: Artificial Sequence
<220> FEATURE:
<223> OTHER INFORMATION: Primer

<400> SEQUENCE: 155
gatctcctag agtcgtgact tggt                                    24

<210> SEQ ID NO 156
<211> LENGTH: 24
<212> TYPE: DNA
<213> ORGANISM: Artificial Sequence
<220> FEATURE:
<223> OTHER INFORMATION: Primer

<400> SEQUENCE: 156
gatctcctag agtcgtgact tggg                                    24

```
<210> SEQ ID NO 157
<211> LENGTH: 24
<212> TYPE: DNA
<213> ORGANISM: Artificial Sequence
<220> FEATURE:
<223> OTHER INFORMATION: Primer

<400> SEQUENCE: 157
gatctcctag agtcgtgact tggc                                              24

<210> SEQ ID NO 158
<211> LENGTH: 37
<212> TYPE: DNA
<213> ORGANISM: Artificial Sequence
<220> FEATURE:
<223> OTHER INFORMATION: Primer

<400> SEQUENCE: 158
ggaaacagct atgaccatcg atctcctaga gtcgtga                                37

<210> SEQ ID NO 159
<211> LENGTH: 36
<212> TYPE: DNA
<213> ORGANISM: Artificial Sequence
<220> FEATURE:
<223> OTHER INFORMATION: Primer

<400> SEQUENCE: 159
tgtaaaacga cggccagtgc tgctagtgtc cgatgt                                 36

<210> SEQ ID NO 160
<211> LENGTH: 18
<212> TYPE: DNA
<213> ORGANISM: Artificial Sequence
<220> FEATURE:
<223> OTHER INFORMATION: Primer

<400> SEQUENCE: 160
tgtaaaacga cggccagt                                                     18

<210> SEQ ID NO 161
<211> LENGTH: 19
<212> TYPE: DNA
<213> ORGANISM: Artificial Sequence
<220> FEATURE:
<223> OTHER INFORMATION: Primer

<400> SEQUENCE: 161
ggaaacagct atgaccatc                                                    19
```